(12) United States Patent
Huang

(10) Patent No.: US 11,275,091 B2
(45) Date of Patent: Mar. 15, 2022

(54) SARS-COV-2 INFECTION BIOMARKERS AND USES THEREOF

(71) Applicant: Children's Hospital Medical Center, Cincinnati, OH (US)

(72) Inventor: Gang Huang, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 17/131,871

(22) Filed: Dec. 23, 2020

(65) Prior Publication Data
US 2021/0325407 A1   Oct. 21, 2021

Related U.S. Application Data

(60) Provisional application No. 63/024,020, filed on May 13, 2020, provisional application No. 63/055,975, filed on Jul. 24, 2020, provisional application No. 63/007,477, filed on Apr. 9, 2020.

(51) Int. Cl.
| | | |
|---|---|---|
| *G01N 33/68* | (2006.01) | |
| *A61K 31/519* | (2006.01) | |
| *A61K 45/06* | (2006.01) | |

(52) U.S. Cl.
CPC ....... *G01N 33/6893* (2013.01); *A61K 31/519* (2013.01); *A61K 45/06* (2013.01); *G01N 2333/5421* (2013.01); *G01N 2333/56* (2013.01); *G01N 2333/57* (2013.01)

(58) Field of Classification Search
None
See application file for complete search history.

(56) References Cited

U.S. PATENT DOCUMENTS

| | | |
|---|---|---|
| 7,598,257 B2 | 10/2009 | Rodgers et al. |
| 7,622,559 B2 | 11/2009 | Teeling et al. |
| 8,142,777 B2 | 3/2012 | Hamilton et al. |
| 8,529,893 B2 | 9/2013 | Welcher et al. |
| 8,722,693 B2 | 5/2014 | Rodgers et al. |
| 8,956,607 B2 | 2/2015 | Osterroth et al. |
| 8,992,920 B2 | 3/2015 | Smith |
| 10,022,378 B2 | 7/2018 | Gavegnano et al. |
| 10,703,814 B2 | 7/2020 | Ellis et al. |
| 11,045,546 B1 | 6/2021 | Kelly et al. |
| 2018/0252727 A1 | 9/2018 | Garfall et al. |
| 2019/0269744 A1 | 9/2019 | Tufaro et al. |
| 2019/0336504 A1 | 11/2019 | Gill et al. |

FOREIGN PATENT DOCUMENTS

| | | |
|---|---|---|
| WO | WO 2014/205132 A2 | 1/2014 |
| WO | WO 2016/035014 A1 | 3/2016 |

OTHER PUBLICATIONS

Lucijanic et al., Leukemia (2021) 35:1218 (Year: 2021).*
Bassetti, M., et al., "The novel Chinese coronavirus (2019-nCoV) infections: Challenges for fighting the storm," Eur J Clin Invest, 2020, 50:e 13209, 4 pgs.
Brudno, J.N., et al., "Toxicities of chimeric antigen receptor T cells: recognition and management," Blood, 2016, 127(26):3321-3330, 10 pgs. https://doi.org/10.1182/blood-2016-04-703751.
Chan, J.K., et al., "Alarmins: awaiting a clinical response," J Clin Invest, 2012, 122(8):2711-2719.
Chen, Z., et al., "T cell responses in patients with COVID-19," Nat Rev Immunol, 2020, 20:529-536, 8 pgs. https://doi.org/10.1038/s41577-020-0402-6.
Chinese Clinical Trial Registry, Index of Versions 1.0-1.7 of Clinical Trial ChiCTR2000029580, 1 pg. http://www.chictr.org.cn/historyversionpuben.aspx?regno=ChiCTR2000029580.
Chinese Clinical Trial, ChiCTR2000029580, Version 1.0, Feb. 8, 2020, 4 pgs. www.chictr.org.cn/hvshowproject.aspx?id=21877.
Egge, K.H., et al., "The anti-inflammatory effect of combined complement and $CD_{14}$ inhibition is preserved during escalating bacterial load," Clin Exp Immunol, 2015, 181:457-467, 11 pgs.
Harrison, C., et al., "JAK Inhibition with Ruxolitinib versus Best Available Therapy for Myelofibrosis," N Engl J Med, 2012, 366:787-798, 29 pgs.
International Search Report and Written Opinion dated May 6, 2021 for Application No. PCT/US2020/066621, 21 pgs.
Bulut, O., et al., "Mesenchymal stem cell derived extracellular vesicles: promising immunomodulators against autoimmune, auto inflammatory disorders and SARS-CoV-2 infection," Turkish Journal of Biology, May 4, 2020, pp. 273-282, 10 pgs.
Clinical Trial NCT04334044 "Treatment of SARS Caused by COVID-19 with Ruxolitinib," ClinicalTrials.com, Apr. 3, 2020, downloaded from https://clinicaltrials.gov/ct2/show/NCT04334044, 7 pgs.
"Compassionate Use Programs—COVID-19," Italian Medicines Agency, Apr. 3, 2020, downloaded from https://www.aifa.gov.it/en/programmi-di-uso-compassionevole-covid-19, 2 pgs.
Kenderian, S.S., et al., "Ruxolitinib Prevents Cytokine Release Syndrome after Car T-Cell Therapy Without Impairing the Anti-Tumor Effect in a Xenograft Model," Abstract 2, Biol Blood Marrow Transplant, 2017, 23:S19-S20, 2 pgs.
"Ruxolitinib Managed Access program (MAP) for patients diagnosed with COVID19 and have severe/very severe lung disease: Guidance and information package," Novartis, Mar. 25, 2020, 10 pgs.
Vannucchi, A.M., et al., "Compassionate use of JAK1/2 inhibitor ruxolitinib for severe COVID-19: a prospective observational study," Leukemia, Aug. 19, 2020, pp. 1-13, 13 pgs.

(Continued)

*Primary Examiner* — Gary B Nickol
*Assistant Examiner* — Jegatheesan Seharaseyon
(74) *Attorney, Agent, or Firm* — Frost Brown Todd LLC; Nicole M. Tepe

(57) ABSTRACT

Disclosed herein are methods that employ the use of one or more biomarkers for the treatment of SARS-CoV-2 infected individuals (COVID-19 patients). The methods may employ detection and measurement of one or more cytokines, the measurement of which may be used to treat COVID-19 patients with one or more immunomodulatory therapies.

4 Claims, 17 Drawing Sheets

(56) References Cited

OTHER PUBLICATIONS

Wang, C-H., et al., "Adjuvant Treatment With a Mammalian Target of Rapamycin Inhibitor, Sirolimus, and Steroids Improves Outcomes in Patients With Severe H1N1 Pneumonia and Acute Respiratory Failure," Critical Care Medicine, 2014, 42:313-321, 9 pgs.
Wang, W., et al., "The definition and risks of Cytokine Release Syndrome-Like in 11 COVID-19-Infected Pneumonia critically ill patients: Disease Characteristics and Retrospective Analysis," medRxiv, preprint Jun. 26, 2020, downloaded from https://www.medrxiv.org/content/10.1101/2020.06.26.20026989v1.fill.pdf, 35 pgs.
International Invitation to Pay Additional Fees and, Where Applicable, Protest Fees, dated Mar. 9, 2021 for Application No. PCT/US2020/066621, 2 pgs.
Ahmed, A., et al. "Ruxolitinib in adult patients with secondary haemophagocytic lymphohistiocytosis: an open-label, single-centre, pilot trial," Lancet Haematol, 2019, 6(12): e630-e7, 8 pgs.
Ajayi, S., et al. "Ruxolitinib," In: Martens U. (eds) Small Molecules in Hematology. Recent Results Cancer Res, Springer, Cham., Springer Nature 2018, pp. 119-132, 14 pgs.
Albeituni, S., et al., "Mechanisms of action of ruxolitinib in murine models of hemophagocytic lymphohistiocytosis," Blood, 2019, 134(2):147-159, 21 pgs.
Andrade, L.P. (ed.), "Coronavirus Edition," Journal of Bioengineering and Technology Applied to Health, SENAI Institute of Innovation in Advanced Health Systems—ISI/SENAI CIMATEC, Mar. 2020, vol. 3, No. 1, 113 pgs. (Filed in two parts. Part 1—66 pgs., Part 2, 47 pgs.).
Applied Stemcell, Inc., Targatt™-HEK293 Master Cell Line & Knock-in Kit, Datasheet, 2020, 9 pgs.
Arnaldez, F.I., et al., "The Society for Immunotherapy of Cancer perspective on regulation of interleukin-6 signaling in COVID-19-related systemic inflammatory response," Journal for ImmunoTherapy of Cancer, 2020, 8:e000930, 12 pgs.
Barosi, G., et al., "Primary myelofibrosis: Older age and high JAK2N617F allele burden are associated with elevated plasma high-sensitivity C-reactive protein levels and a phenotype of progressive disease," Leuk Res, 2017, 60:18-23, 6 pgs.
Blanco-Melo, D., et al. "Imbalanced Host Response to SARS-CoV-2 Drives Development of COVID-19," Cell, 2020, 181:1036-1045, 20 pgs.
Cao, B., et al., "A Trial of Lopinavir-Ritonavir in Adults Hospitalized with Severe Covid-19," N Engl J Med, 2020, 382(19):1787-1799, 13 pgs.
Cao, Y., et al., "Cytokines profiling and their clinical significance analysis of 2019-nCoV pneumonia patients," Tongji Hospital, Tongji Medical College, Hiazhong University of Science and Technology, Wuhan, Hubei, China, Feb. 5, 2020, 3 pgs.
Cao, Y., et al., "Cytokines profiling and their clinical significance analysis of 2019-nCoV pneumonia (novel coronavirus pneumonia, NCP) patients," Tongji Hospital, Tongji Medical College, Hiazhong University of Science and Technology, Wuhan, Hubei, China, Feb. 8, 2020, 3 pgs.
Cao, Y., et al., "Cytokines profiling and their clinical significance analysis of novel coronavirus pneumonia (COVID-19) patients," Tongji Hospital, Tongji Medical College, Hiazhong University of Science and Technology, Wuhan, Hubei, China, Feb. 12, 2020, 3 pgs.
Cao, Y., et al., "Cytokines profiling and their clinical significance analysis of novel coronavirus pneumonia (COVID-19) patients," Tongji Hospital, Tongji Medical College, Hiazhong University of Science and Technology, Wuhan, Hubei, China, Feb. 24, 2020, 3 pgs.
Cao, Y., et al., "Imaging and clinical features of patients with 2019 novel coronavirus SARS-CoV-2: A systematic review and meta-analysis," J Med Virol, 2020, 11 pgs.
Cao, Y., et al., "Ruxolitinib in treatment of severe coronavirus disease 2019 (COVID-19): A multicenter, single-blind, randomized controlled trial," J Allergy Clin Immunol, 2020, 146:137-146, 13 pgs.
Cao, Y., "Severe novel coronavirus pneumonia (COVID-19) patients treated with ruxoliitinib in combination with mesenchymal stem cells: a prospective, single blind, randomized controlled clinical trial," Tongji Hospital, Tongji Medical College, Hiazhong University of Science and Technology. Wuhan, Hubei, China, Mar. 9, 2020, 3 pgs.
Chan, J.F-W., et al., "A familial cluster of pneumonia associated with the 2019 novel coronavirus indicating person-to-person transmission: a study of a family cluster," Lancet, Jan. 24, 2020, 395:513-523, 10 pgs.
Channappanavar, R., et al., "Pathogenic human coronavirus infections: causes and consequences of cytokine storm and immunopathology," Semin Immunopathol, 2017, 39(5): 529-539, 11 pgs.
Chen, H., et al., "Management of cytokine release syndrome related to CAR-T cell therapy," Front Med, 2019, 13(5):610-617, 8 pgs.
Chen, N., et al., "Epidemiological and clinical characteristics of 99 cases of 2019 novel coronavirus pneumonia in Wuhan, China: a descriptive study," Lancet, 2020, 395(10223): 507-513, 7 pgs.
Chien, J-Y., et al., "Temporal changes in cytokine/chemokine profiles and pulmonary involvement in severe acute respiratory syndrome," Respirology, 2006, 11(6):715-722, 8 pgs.
China National Health Commission. Diagnosis and treatment of pneumonitis caused by new coronavirus (trial version 5). Beijing: China National Health Commission, http://www.nhc.gov.cn/yzygj/s7653p/202002/3b09b894ac9b4204a79db5b8912d4440.shtr., Feb. 2020, 3 pgs.
Cooper, A.M., et al., "IL-12p40: an inherently agonistic cytokine," Trends Immunol, 2007, 28(1):33-38, 6 pgs.
Crayne, C.B., et al., "The Immunology of Macrophage Activation Syndrome," Front Immunol, 2019; vol. 10, article: 119, 11 pgs.
Das, R., et al., "Janus kinase inhibition lessens inflammation and ameliorates disease in murine models of hemophagocytic lymphohistiocytosis," Blood, 2016, 127(13):1666-1675, 10 pgs.
Du, Y., et al., "Clinical Features of 85 Fatal Cases of COVID-19 from Wuhan: A Retrospective Observational Study," Am J Respir Crit Care Med, Jun. 1, 2020, 201(11):1372-1379, 8 pgs.
Gennaro, A.R., (ed.), Remington's Pharmaceutical Sciences, 18$^{th}$ edition, Mack Publishing Company, Easton, Pennsylvania, 1990, 8 pgs. [Table of Contents Only.].
Gennaro, A.R., (ed.) Remington: The Science and Practice of Pharmacy, 19$^{th}$ edition, Mack Publishing Company, Easton, Pennsylvania, 1995, 3 pgs. [Table of Contents Only.].
Gennaro, A.R., (ed.) Remington: The Science and Practice of Pharmacy, 20$^{th}$ edition, Lippincott Williams & Wilkins, 2000, 5 pgs. [Table of Contents Only.].
Greenfield, G., et al., "The ruxolitinib effect: understanding how molecular pathogenesis and epigenetic dysregulation impact therapeutic efficacy in myeloproliferative neoplasms," J Transl Med, 2018. 16(1):360, 16 pgs.
Gu, J., et al., "Multiple organ infection and the pathogenesis of SARS," J Exp Med, 2005, 202(3):415-424, 10 pgs.
Guan, W., et al., "Clinical Characteristics of Coronavirus Disease 2019 in China," N Engl J Med, Feb. 28, 2020, 13 pgs.
Harrison, C., et al., "Ruxolitinib: a potent and selective Janus kinase 1 and 2 inhibitor in patients with myelofibrosis. An update for clinicians," Ther Adv Hematol, 2012, 3(6):341-354, 14 pgs.
Hechinger, A-K., et al., "Therapeutic activity of multiple common γ-chain cytokine inhibition in acute and chronic GVHD," Blood, 2015, 125(3):570-580, 11 pgs.
Huang, C., et al., "Clinical features of patients infected with 2019 novel coronavirus in Wuhan, China," Lancet, 2020, 395(10223):497-506, 10 pgs.
Huang, R., et al., "HIF1A is a critical downstream mediator for hemophagocytic lymphohistiocytosis," Haemotologia, 2017, 102(11):1956-1968, 13 pgs.
Khwaja, A., "KDIGO Clinical Practice Guidelines for Acute Kidney Injury," Nephron Clin Pract, 2012, 120(4):c179-c184, 6 pgs.
Kotch, C., et al., "Tocilizumab for the treatment of chimeric antigen receptor T cell-induced cytokine release syndrome," Expert Rev Clin Immunol, 2019, 15(8): 813-822, 10 pgs.
Kupferschmidt, K., et al., "Race to find COVID-19 treatments accelerates," Science Mar. 27, 2020; 367(6485):1412-1413, 2 pgs.

(56) References Cited

OTHER PUBLICATIONS

Lai, C-C., et al., "Asymptomatic carrier state, acute respiratory disease, and pneumonia due to severe acute respiratory syndrome coronavirus 2 (SARS-CoV-2): Facts and myths," J Microbiol Immunol Infect, 2020, 53:404-412, 9 pgs.

Lee, D.W., et al., "Current concepts in the diagnosis and management of cytokine release syndrome," Blood, 2014, 124(2):188-195, Erratum in: Blood. Aug. 20, 2015;126(8):1048, 9 pgs.

Li, Q., et al., "Early Transmission Dynamics in Wuhan, China, of Novel Coronavirus-Infected Pneumonia," N Engl J Med, 2020, 382(13):1199-1207, 9 pgs.

Liang, W., et al., "Development and Validation of a Clinical Risk Score to Predict the Occurrence of Critical Illness in Hospitalized Patients With COVID-19," JAMA Internal Medicine, 2020, 180(8):1081-1089, 9 pgs.

Mahallawi, W.H., et al., "MERS-CoV infection in humans is associated with a pro-inflammatory Th1 and Th17 cytokine profile," Cytokine, 2018, 104:8-13, 6 pgs.

Mahase, E., "Covid-19: WHO declares pandemic because of "alarming levels" of spread, severity, and inaction," BMJ, 2020, 368:m1036, 1 pg.

Meng, G., et al., "Ruxolitinib treatment for SR-aGVHD in patients with EBV-HLH undergoing allo-HSCT," Ann Hematol, 2020, 99(2):343-349, 7 pgs.

Menten, P., et al., "Macrophage inflammatory protein-1," Cytokine Growth Factor Rev, 2002, 13(6):455-481, 27 pgs.

Neelapu, S.S., et al., "Chimeric antigen receptor T-cell therapy—assessment and management of toxicities," Nat Rev Clin Oncol, 2018, 15(1):47-62, 37 pgs.

Novartis, "clinical study of Jakavi® in severe COVID-19 patients and establish international compassionate use program," Press Release, Apr. 2, 2020, 7 pgs.

Olsson, A-K., et al., "VEGF receptor signalling—in control of vascular function," Nat Rev Mol Cell Biol, 2006, 7(5):359-371, 14 pgs.

Ouedraogo, D-D., et al., "COVID-19, chronic inflammatory rheumatic disease and anti-rheumatic treatments," Clinical Rheumatology, 2020, 39:2069-2075, 7 pgs.

Pan, F., et al., "Time Course of Lung Changes On Chest CT During Recovery From Novel Coronavirus (COVID-19) Pneumonia," Radiology, 2020, 295(3):715-721, 15 pgs.

Peiris, J.S.M., et al., "Clinical progression and viral load in a community outbreak of coronavirus-associated SARS pneumonia: a prospective study," Lancet, 2003; 361(9371): 1767-1772, 6 pgs.

Przepiorka, D., et al., "FDA Approval Summary: Ruxolitinib for Treatment of Steroid-Refractory Acute Graft-Versus-Host Disease," The Oncologist, 2020, 25:e328-e334, 7pgs.

Ranieri, V.M., et al., "Acute Respiratory Distress Syndrome: The Berlin Definition," JAMA, 2012, 307(23):2526-2533, 8 pgs.

Rudd, K.E., et al., "Association of the Quick Sequential (Sepsis-Related) Organ Failure Assessment (qSOFA) Score with Excess Hospital Mortality in Adults with Suspected Infection in Low- and Middle-Income Countries," JAMA, 2018, 319(21):2202-2211, 10 pgs.

Schulz, O., et al., "Chemokines and Chemokine Receptors in Lymphoid Tissue Dynamics," Annu Rev Immunol, 2016, 34:203-242, 42 pgs.

Sin, J.H., et al., "Ruxolitinib for secondary hemophagocytic lymphohistiocytosis: First case report," Hematol Oncol Stem Cell Ther, 2019, 12:166-170, 5 pgs.

Stebbing, J., et al., "COVID-19: combining antiviral and anti-inflammatory treatments," Lancet Infect Dis, Apr. 2020, 30:400-402, 3 pgs.

Tefferi, A., et al., "Circulating Interleukin (IL)-8, IL-2R, IL-12, and IL-15 Levels Are Independently Prognostic in Primary Myelofibrosis: A Comprehensive Cytokine Profiling Study," J Clin Oncol, 2011, 29(10):1356-1363, 8 pgs.

Trantham, T., et al., "Ruxolitinib for the treatment of lymphoma-associated hemophagocytic lymphohistiocytosis: A cautionary tale," J Oncol Pharm Practice, 2020, 26(4):1005-1008, 4 pgs.

Wang, C-H., et al., "Persistence of lung inflammation and lung cytokines with high-resolution CT abnormalities during recovery from SARS," Respir Res, 2005, 6:42, 12 pgs.

Wang, D., et al., "Clinical Characteristics of 138 Hospitalized Patients With 2019 Novel Coronavirus-Infected Pneumonia in Wuhan, China," JAMA, 2020, 323(11):1061-1069, 9 pgs.

Wang, Y., et al., "Clinical Outcomes in 55 Patients With Severe Acute Respiratory Syndrome Coronavirus 2 Who Were Asymptomatic at Hospital Admission in Shenzhen, China," J Infect Dis, 2020, XX:1-5, 5 pgs.

Wang, J., et al., "Ruxolitinib for refractory/relapsed hemophagocytic lymphohistiocytosis," Haematologica, 2020, 105:e210-e212, 3 pgs.

Wen, X., et al., "Integration of Prealbumin into Child-Pugh Classification Improves Prognosis Predicting Accuracy in HCC Patients Considering Curative Surgery," Journal of Clinical and Translational Hepatology, 2018, 6(4):377-384, 8 pgs.

Wong, C.K., et al., "Plasma inflammatory cytokines and chemokines in severe acute respiratory syndrome," Clin Exp Immunol, 2004, 136(1):95-103, 9 pgs.

World Health Organization, Clinical management of severe acute respiratory infection when novel coronavirus (2019-nCoV) infection is suspected: interim guidance, Jan. 28, 2020. Geneva: World Health Organization; 2020. Ref No. WHO/nCoV/Clinical/2020.3, 10 pgs.

World Health Organization, Coronavirus disease (COVID-2019) R&D. Geneva: http://www.who.int/blueprint/priority-diseases/key-action/novel-coronavirus/en/, 2020, 10 pgs.

Xu, Z., et al., "Pathological findings of COVID-19 associated with acute respiratory distress syndrome," Lancet Respir Med, 2020, 8:420-422, 3 pgs.

Yan, X., et al., "Evolution characteristics of thoracic lesions of CT of COVID-19 in recovery stage," Radiologic Practice, Apr. 2020, 35(4):428-432, 5 pgs.

Yao, X., et al., "A pathological report of three COVID-19 cases by minimally invasive autopsies," Clin J Pathol, May 2020, 49(5):411-418, 8 pgs.

Zandvakili, I., et al., "Ruxolitinib as first-line treatment in secondary hemophagocytic lymphohistiocytosis: A second experience," AJH Wiley, 2018, pp. E123-E125, 3 pgs.

Zhang, C., et al., "Cytokine release syndrome in severe COVID-19: interleukin-6 receptor antagonist tocilizumab may be the key to reduce the mortality," Int J Antimicrob Agents, 2020, 55:105954, 6 pgs.

Zhang, L., et al., "D-dimer levels on admission to predict in-hospital mortality in patients with Covid-19," Journal of Thrombosis and Haemostasis: JTH, 2020, 18 pgs.

Zhang, Q., et al., "Clinical trial analysis of 2019-nCoV therapy registered in China," J Med Virol, 2020, 92:540-545, 6 pgs.

Zhang, W., et al., "The use of anti-inflammatory drugs in the treatment of people with severe coronavirus disease 2019 (COVID-19): The Perspectives of clinical immunologists from China," Clinical Immunology, 2020, 214:108393, 5 pgs.

Zhang, Y., et al., "Analysis of Serum Cytokines in Patients with Severe Acute Respiratory Syndrome," Infect Immun, 2004, 72(8):4410-4415, 6 pgs.

Zhonghua, [Chinese guidelines for the diagnosis and treatment of heart failure 2018], Chin J Cardiol, 2018;46(10):760-789, 30 pgs. [Chinese language only.].

Zhou, X., et al., "Recurrent pneumonia in a patient with new coronavirus infection after discharge from hospital for insufficient antibody production: a case report," BMC Infectious Diseases, 2020, 20:500, 4 pgs.

Zhu, N., et al., "A Novel Coronavirus from Patients with Pneumonia in China, 2019," N Engl J Med, 2020, 382(8):727-733, 7 pgs.

Zhu, R., et al., "Systematic Review of the Registered Clinical Trials of Coronavirus Diseases 2019 (COVID-19)" medRxiv, Mar. 2020, 24 pgs.

Adnkronos, "Coronavirus, first positive outcomes from "anti-intensive care" drug," downloaded from www.adnkronos.com/coronavirus-primi-esiti~positivi-da—farmaco-anti-terapie-intensive_kzSP7ino7VvSyEDTNJ96d, Published Mar. 28, 2020, 3 pgs. (Google translated from Italian).

(56) References Cited

OTHER PUBLICATIONS

Bhaskar, S., et al., "Cytokine Storm in COVID-19-Immunopathoioigical Mechanisms, Clinical Considerations, and Therapeutic Approaches: The REPROGRAM Consortium Position Paper," Front Immunol, Hypothesis and Theory, Jul. 10, 2020, 11(Article 1648):1-16, 16 pgs.

Chen, L., et al., "Elevated serum levels of S100A8/A9 and HMGB1 at hospital admission are correlated with inferior clinical outcomes in COVID-19 patients," Cellular & Molecular Immunology, Jul. 3, 2020, 17:992-994, 3 pgs.

Clinical Trial NCT04331665, "Study of the Efficacy and Safety of Ruxolitinib to Treat COVID-19 Pneumonia," ClinicalTrials.gov, U.S. National Library of Medicine, Apr. 2, 2020, downloaded from https;//clinicaltrials.gov/ct2/show/NCT04331665?term=NCT04331665&draw=2&rank=1, 6 pgs.

Clinical Trial NCT04337359, "Ruxolitinib Managed Access Program (MAP) for Patients Diagnosed With Severe/Very Severe COVID-19 Illness," ClinicalTrials.gov, U.S. National Library of Medicine, Apr. 3, 2020, downloaded from https://clinicaltrials.gov/ct2/show/NCT04337359?term=nct04337359&draw=2&rank=1, 5 pgs.

Clinical Trial NCT04338958, "Ruxolitinib in COVID-19 Patients With Defined Hyperinflammation (RuxCoFlam)," ClinicalTrials.gov, U.S. National Library of Medicine, Apr. 8, 2020, downloaded from https://clinicaltrials.gov/ct2/show/NCT04338958?term=NCT04338958&draw=2&rank=1, 7 pgs.

Clinical Trial NCT04377620, "Assessment of Efficacy and Safety of Ruxolitinib in Participants With COVID-19-Associated ARDS Who Require Mechanical Ventilation (RUXCOVID-DEVENT)," ClinicalTrials.gov, U.S. National Library of Medicine, May 6, 2020, downloaded from https:/www.clinicaltrials.gov/ct2/show/NCT043777620, 7 pgs.

Hu, B., et al., "The cytokine storm and COVID-19," J Med Virol, Jun. 27, 2020, 93:250-256, 24 pgs.

Incyte, "Incyte Announces Results from the Phase 3 DEVENT Study Evaluating Ruxolitinib (Jakafi ®) as a Treatment for Patients with COVID-19 Associated Acute Respiratory Distress Syndrome (ARDS) on Mechanical Ventilation," Incyte.com, Mar. 18, 2021, downloaded from https://investor.incyte.com/press-releases/press-releases/2021/Incyte-Announces-Results-from-the-Phase-3-DEVENT-Study-Evaluating-Ruxolitinib-Jakafi-as-a-Treatment-for-Patients-with-COVID-19-Associated-Acute-Respiratory-Distress-Syndrome-ARDS-on-Mechanical-Ventilation/default.aspx, 6 pgs.

Incyte. "Incyte COVID-19 Response," Incyte.com, Jun. 11, 2021, downloaded from https://www.incyte.com/COVID-19, 6 pgs.

Ingraham, N., et al., "Immunomodulation in COVID-19," The Lancet Respiratory Medicine, May 4, 2020, 8:544-546, 3 pgs.

Malavolta, M., et al., "Exploring the Relevance of Senotherapeutics for the Current SARS-CoV-2 Emergency and Similar Future Global Health Threats," Cells, Apr. 8, 2020, 9:909, 12 pgs.

Novartis, "Novartis provides update on RUXCOVID study of ruxolitinib for hospitalized patients with COVID-19," Novartis.com, Dec. 14, 2020, downloaded from https://www.novastis.com/news/media-releases/novartis-provides-update-ruxcovid-study-ruxolitinib-hospitalized-patients-covid-19?_ga=2.14653567.917090364.1629207225-2081311836.1629207225, 7 pgs.

Shi, H., et al., "Neutrophil calprotectin identifies severe pulmonary disease in COVID-19," medRxiv, Jul. 15, 2020, 20 pgs.

Sohn, K., et al., "COVID-19 patients upregulate toll-like receptor 4-mediated inflammatory signaling that mimics bacterial sepsis," bioRxiv, Jul. 17, 2020, 26 pgs.

Australian Office Action, Examination report No. 1 for standard patent application, dated Jun. 25, 2021 for Application No. AU 2021201783, 10 pgs.

Australian Office Action, Examination report No. 1 for standard patent application, dated Jul. 12, 2021 for Application No. AU 2021201786, 9 pgs.

Gaspari, V., et al., "Side effects of ruxolitinib in patients with SARS-CoV-2 infection: Two case reports," International Journal of Antimicrobial Agents, 2020, 56(2):106023, 2 pg.s.

Gozzetti, A., et al., "The Janus kinase 1/2 inhibitor ruxolitinib in COVID-19," Leukemia, 2020, 34:2815-2816, 2 pgs.

Hasselbalch, H.C., et al., "COVID-19 as a mediator of interferon deficiency and hyperinflammation: Rationale for the use of JAK1/2 inhibitors in combination with interferon," Cytokine and Growth Factor Reviews, 2021, 60:2845, 18 pgs.

Incyte, "Incyte Announces Plans to Initiate a Phase 3 Clinical Trial of Ruxolitinib (Jakafi®) as a Treatment for Patients with COVID-19 Associated Cytokine Storm," Business Wire, Incyte Press Release Apr. 2, 2020, downloaded Aug. 10, 2021 from https://www.businesswire.com/news/hone/20200402005731/en/Incyte-Announces-Plans-to-Initiate-a-Phase-3-Clinical-Trial-of-Ruxolitinib-Jakafi-as-a-Treatment-for- Patients-with-COVID-19-Associated-Cytokine-Storm, 4 pgs.

La Rosee, F., et al., "The Janus kinase 1/2 inhibitor ruxolitinib in COVID-19 with severe systemic hyperinflammation," Leukemia, 2020, 34:1805-1815, 11 pgs.

Tisoncik, J.R., et al., "Into the Eye of the Cytokine Storm," Microbiology and Molecular Biology Reviews, 2012, 76(1):16-32, 17 pgs.

European Search Report, Extended, and Written Opinion dated Aug. 18, 2021 for Application No. EP 21167502.0, 9 pgs.

European Search Report, Partial, and Provisional Written Opinion dated Aug. 31, 2021 for Application No. EP 21167513.7, 14 pgs.

Chen, L., et al., "Scoring cytokine storm by the levels of MCP-3 and IL-8 accurately distinguished COVID-19 Patients with high mortality," Signas Transduction and Targeted Therapy, 2020, 5:292, 3 pgs.

Chen, G., et al., "Clinical and immunological features of severe and moderate coronavirus disease 2019," J Clin Invest, 2020, 130(5):2620-2629, 10 pgs.

Lee, W. J., et al., "Are Prognostic scores and biomarkers such as procalcitonin the appropriate prognostic precursors for elderly patients with sepsis in the emergency department?" Aging Clin Exp Res, 2016, 28:917-924, 8 pgs.

Sun, D., et al., "Clinical features of severe pediatric patients with coronavirus disease 2019 in Wuhan: a single center's observational study," World Journal of Pediatrics, 2020, 16:251-259, 9 pgs.

European Search Report, Extended, and Written Opinion dated Dec. 14, 2021 for Application No. EP 21167513.7, 17 pgs.

\* cited by examiner

SARS-COV-2 INFECTION BIOMARKERS AND USES THEREOF

CROSS-REFERENCE TO RELATED APPLICATIONS

This application claims priority to and benefit of U.S. Provisional Patent Application Ser. No. 63/007,477, filed Apr. 9, 2020, entitled "Compositions and Methods for the Treatment of Severe Acute Respiratory Syndrome Coronavirus 2 (SARS-COV-2) Infection," U.S. Provisional Patent Application Ser. No. 63/024,020, filed May 13, 2020, entitled "SARS-COV-2 Infection Biomarkers and Uses Thereof," and U.S. Provisional Patent Application Ser. No. 63/055,975, filed Jul. 24, 2020, entitled "SARS-COV-2 Infection Biomarkers and Uses Thereof," the contents of which are incorporated by reference in their entirety for all purposes.

BACKGROUND

The end of 2019 witnessed an outbreak of severe acute respiratory syndrome coronavirus 2 (SARS-CoV-2) infection and its associated coronavirus disease 2019 (COVID-19) in Wuhan, China[1,2]. Its rapid global spread has been classified as a pandemic by the World Health Organization[3] and now represents one the most serious issues to public health globally. COVID-19 is a heterogeneous disease population, of which most patients exhibit mild to moderate symptoms, but around 15% progress to severe pneumonia and about 5% are eventually admitted to the intensive care unit (ICU) due to acute respiratory distress syndrome (ARDS), septic shock and/or multiple organ failure. To this end, while a majority of individuals having COVID-19 have self-limited disease course, ICU patients respond poorly to currently available treatments, and have a high mortality. Two major obstacles to improve the clinical outcome in these patients are inadequate acknowledgement of determinant cytokines driving the fatal deterioration, and inability to identify an individual patient with high risk of ICU admission and fatal outcome. Tremendous efforts had been taken to address the critical issues mentioned above.

Aberrant immune response, also referred as 'cytokine storm', is featured in severe SARS-CoV-2 infection and proposed to associate with inferior clinical prognosis and also lethal multiple organ dysfunction syndrome[6-8]. Given the proposed key pathophysiological role of cytokine storm in the severe/critically ill COVID-19, assessment of treatments using existing immunomodulatory agents, in addition to vaccine and antiviral agents, has become a major focus for improving clinical outcome by dampening an excessive inflammatory response before it leads to irreversible immune-mediated damage. Clinically, immunomodulatory therapies that target the deleterious effects of cytokine storm have achieved great clinical success in the treatment of steroid-refractory acute graft-versus-host disease (SR-aGVHD) after allogeneic hematopoietic stem cell transplantation or secondary hemophagocytic lymphohistiocytosis.

Although a number of immunomodulation therapies, such as targeted therapies against IL-6, IL-1, TNFα, JAK/STAT pathway and GM-CSF, etc., are now being actively tested, several critical issues on cytokine storm in COVID-19 remain to be addressed. Previous studies had shown remarkably increased serum levels of the pro-inflammatory IL-6, IL-10 and TNF-a, and notable CD4+ and the CD8+T cytopenia in COVID-19 patients. Moreover, patients requiring ICU admission had higher concentrations of G-CSF, IP10, MCP-1, MIP-1α, and TNFα than those did not. Although these studies had proposed different spectrum of pro-inflammatory cytokines linked to inferior outcomes in COVID-19 patients, the determinant cytokines to drive clinically meaningful cytokine storm have been inconclusive. Lacking a reliable quantitative method able to compute the severity of cytokine storm has made it difficult to guide clinical management based on the immunopathological findings. Identification of the important cytokines, developing a uniform evaluation standard of cytokine storm is hence important to optimization of clinical management of COVID-19 patients. The instant disclosure seeks to address one or more of the aforementioned needs in the art.

BRIEF SUMMARY

Disclosed herein are methods that employ the use of one or more biomarkers for the treatment of SARS-CoV-2 infected individuals, specifically, individuals having COVID-19. The methods may employ detection and measurement of one or more cytokines, the measurement of which may be used to treat COVID-19 patients with one or more immunomodulatory therapies. More particularly, the disclosed methods may be used to identify patients having COVID-19 who are at higher risk of developing severe symptoms requiring intensive care unit (ICU) care.

BRIEF DESCRIPTION OF THE DRAWINGS

This application file may contain at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

DETAILED DESCRIPTION

Definitions and Abbreviations

Figure 1:
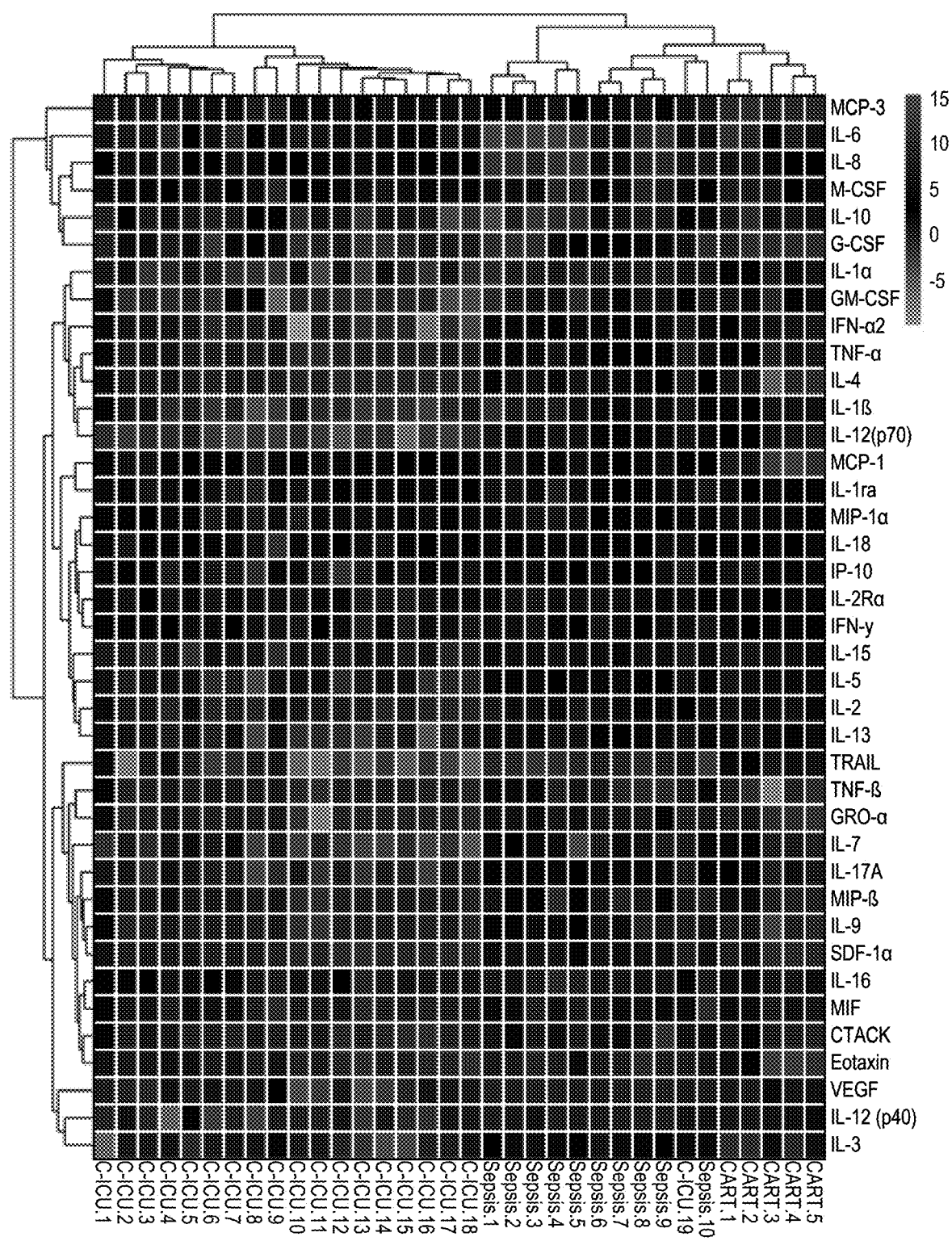
FIG. 1. Unsupervised clustering analysis of average baseline-adjusted and log 2-transformed fold change of cytokines in COVID-19 infected patients needing ICU admission, sepsis patients, and patients who were experiencing CRS after receiving CART cell therapy. The presented 39 cytokines/chemokines are overlapped ones in all the three sets of data. C-ICU, COVID-19 patients in ICU wards; Sepsis, bacterial septicemia.

Unless otherwise noted, terms are to be understood according to conventional usage by those of ordinary skill in the relevant art. In case of conflict, the present document, including definitions, will control. Exemplary methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

Abbreviations: COVID-19: Coronavirus Disease 2019; SARS-CoV-2: Severe Acute Respiratory Syndrome coronavirus 2; ARDS: Acute respiratory Distress Syndrome; ICU: Intensive Care Unit; IL: interleukin; IP-10: Interferon gamma induced protein 10; MCP: Monocyte chemotactic protein; MIP-1α: Macrophage inflammatory protein 1 alpha; IFN-γ: Interferon gamma; M-CSF: Macrophage colony stimulating factor; β-NGF: Beta-nerve growth factor; HGF: Hepatocyte growth factor; SCF: Stem cell factor; RANTES: CCL5, a member of the CC family of chemokines; GM-CSF: Granulocyte-macrophage colony-stimulating factor; TRAIL: TNF-related apoptosis-inducing ligand.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

The active agent may form salts, which are also within the scope of the preferred embodiments. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts")

may be formed and are included within the term "salt(s)" as used herein. Pharmaceutically acceptable (e.g., non-toxic, physiologically acceptable) salts are preferred, although other salts are also useful, e.g., in isolation or purification steps, which may be employed during preparation. Salts of the compounds of the active agent may be formed, for example, by reacting a compound of the active agent with an amount of acid or base, such as an equivalent amount, in a medium such as one in which the salt precipitates or in an aqueous medium followed by lyophilization. When the compounds are in the forms of salts, they may comprise pharmaceutically acceptable salts. Such salts may include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

Cytokine storm is featured in severe/critically ill COVID-19 patients and proposed to correlate with inferior clinical prognosis. A number of immunomodulation therapies are being actively tested to improve clinical outcome by dampening excessive inflammatory responses. However, lacking a uniform quantitative standard to evaluate the severity of cytokine storm is a major obstacle to guiding clinical management by immunopathological manifestations. Disclosed herein are methods useful for optimizing current clinical management of COVID-19.

Disclosed herein are biomarker systems that may be used to direct treatment of an individual having COVID-19. For example, the individual may be one who is categorized as a "Group 3" COVID-19 patient, such that a treatment may be administered to prevent such patient's advancement to "Group 4" so as to avoid requiring ICU treatment. In certain aspects, biomarker measurement may be used, as described herein, to improve outcomes of COVID-19 patients.

In one aspect, a method of treating an individual having, or suspected of having a SARS-Cov-2 infection (COVID-19) is disclosed. In one aspect, the disclosed methods may be used to treat an individual having COVID-19 who presents with the symptoms of cytokine storm, or is believed to be at risk for developing cytokine storm. In this aspect, the method may comprise categorizing an individual as "likely to require Intensive Care Unit (ICU) care" or "not likely to require ICU care," comprising assaying one or more cytokines from a biological sample obtained from the individual. The biological sample may be blood, or serum, for example, but may further include any biological sample obtained from the individual that can be used to ascertain the level of one or more of the cytokines as described herein, such as urine or saliva. Samples may be collected from hospitalized patients, and the disclosed biomarkers/cytokines measured as early as the point right after hospitalization (usually 1-2 weeks after infection). Individuals just testing positive, as early as 2-3 days after infection, may not benefit from testing of cytokine levels, as 80-85% of infected people have self-limited disease and do not need further testing or treatment.

The disclosed methods may be best employed with those having severe symptoms (such as cytokine storm). The disclosed methods allow for targeted immunomodulation treatment for high risk patients and may allow for early identification of hospitalized patients who are at high risk for ICU admission, or who have high risk of death even in the regular ward. That is, the disclosed biomarker panels allow identification of high-risk groups of hospitalized severe COVID-19 patients that are best suited for immunomodulation therapy, which in turn minimizes risk of progression to ICU and death. Said yet another way, the disclosed methods allow identification of potential "group 4"/ICU patients and, by administering immunoglobulin treatment, keep such patients within "group 3"/hospitalized patients for eventual recovery. Anti-viral therapy, like Remdevir, may not be of significant therapeutic use at the late stage severe form COVID-19 when they have low or even undetectable virus load, but may be advantageous at an earlier time point (such as right after hospitalization).

In certain aspects, the cytokines may be selected from one or more of MCP-3, IL-8, IFN-α2 and IFN-γ. In one aspect, if MCP-3 is elevated, and/or if IL-8 is elevated, or if the IFN-α2/IFN-γ ratio is decreased in said individual, the individual may be categorized as likely to require ICU care and is administered the appropriate therapy, for example, an immunomodulation therapy as described herein.

In one aspect, a method of treating an individual having, or suspected of having, a SARS-Cov-2 infection (COVID-19) is disclosed. In this aspect, the method may comprise detecting one or more cytokines selected from calprotectin (S100A8/A9), HMGB1, MCP-3, IL-8, and combinations thereof in a sample obtained from the individual, and determining the probability or risk that the individual will require intensive care unit (ICU) care based on the cytokine levels. In one aspect, if the individual has an increased risk of requiring intensive care unit (ICU) care, a therapeutically effective amount of an immunomodulation therapy is administered to the individual. In one aspect, S100A9/A9 is detected in the individual, and if an increase in S100A8/A9 is detected, the individual is identified as having an increased risk of requiring ICU care and provided the appropriate treatment. In one aspect, the cytokines detected are S100A9/A9 and HMGB1. In one aspect, MCP-3 and IL-8 are detected. IN a further aspect, the detected cytokines are selected from MCP-3, IL-8, IFN-α2 and IFN-γ.

Based on the levels of one or more of the aforementioned cytokines, an individual is characterized as likely or not likely to require ICU care, and treated accordingly, wherein an individual characterized as likely to require ICU care, in one exemplary embodiment, is provided an immunomodulation therapy. For example, if MCP-3 or IL-8 are elevated as compared to a control value, the individual is identified as having an increased risk of requiring ICU care and is administered in immunomodulation therapy that may include, for example, ruxolitinib. A high MCP-3/IL-8 score generally indicates a cytokine storm state which represents an imbalance of immune response, which also correlates with a low type I interferon (IFN-a2, an early immune response marker) and high type II interferon (IFN-γ, a late immune response marker). The disclosed methods allow an alternative means for detecting an imbalance of immune response to the virus infection of this high-risk group of patients.

In one aspect, the method may comprise assaying IFN-α2 and IFN-γ in a COVID-19 patient (suspected or confirmed) and calculating a IFN-α2/IFN-γ ratio wherein if the IFN-α2/IFN-γ ratio is lower than that of a control value (a non-limiting control value may be that of an individual that does not have COVID-19), said individual is treated as an individual likely to require ICU care. Such individual may be administered an immunomodulation therapy such as ruxolitinib.

In one aspect, the methods may further include detecting one or more cytokines selected from one or more of MCP1, MIP-1α, MIP-1β, IL-1Rα, IL-2Rα, IL-5, IL-15, IL-18, LIF, M-CSF, TNF-β, HGF, SCF, SCGF-β, IL-1α, IL-7, IL-12, RANTES, GM-CSF, TRAIL; wherein an increase in one or more of MCP1, MIP-1α, MIP-1β, IL-1Rα, IL-2Rα, IL-5, IL-15, IL-18, LIF, M-CSF, TNF-β, HGF, SCF and SCGF-β and/or a decrease in one or more of IL-1α, IL-7, IL-12, RANTES, GM-CSF, or TRAIL indicates that said individual may be a candidate for immunomodulation therapy; and wherein if said individual is diagnosed as a candidate for immunomodulation therapy, an immunomodulation therapy may be administered to said individual.

In one aspect, disclosed is a method for identifying an individual likely to need intensive care unit (ICU) care. In this aspect, the method may comprise detecting one or more inflammatory cytokines, wherein an increase in IL-8, IP-10, MCP-1, MCP-3, MIP-1α, IL-1α, IL-1Rα, IL-6, IL-10, IL-16, IL-17A, IL-18, IFN-γ, M-CSF, β-NGF, HGF, and SCF and a decrease in RANTES, GM-CSF and TRAIL indicates that an individual is likely to need ICU care.

In one aspect, disclosed is a method for identifying an individual having, or likely to have, cytokine storm in an individual having, or suspected of having, a SARS-Cov-2 infection (COVID-19). In this aspect, the method may comprise determining a level of IFNα2, IFNγ, IL-6, MCP-3, TNFα, IL-1β, IL-2, IL-12 and GM-CSF, wherein low levels of IFNα2, elevated levels of IFNγ, IL-6, and MCP-3, and normal levels of TNFα, IL-1β, IL-2, IL-12 and GM-CSF may indicate an individual likely to have COVID-19 associated cytokine storm. In this aspect, the individual identified as having, or likely to have, cytokine storm may then be treated with an immunomodulation therapy.

In one aspect, disclosed is a method for treating a confirmed or likely COVID-19 positive individual. In this aspect, the method may comprise classifying said individual as an likely to be an Intensive Care Unit (ICU) patient or as not likely to be an Intensive Care Unit (ICU) patient. In this aspect, the classification may be determined based on assaying a level of a cytokine in the blood of said individual, selected from one or more of MCP-3, IL-8, IL-6, MCP-1, IL-10, RANTES, HGF, and β-NGF, and optionally one or more of IL-1rα, and IL-1α, IL-2 and IL-1β; wherein when if one or more of MCP-3, IL-8, IL-6, MCP-1, IL-10, HGF, β-NGF, IL-1rα, and IL-1α, IL-2 and IL-1β are increased, or if RANTES 15 decreased, said individual is likely to be an ICU patient; and wherein said individual likely to be an ICU patient may be administered appropriate care, for example, an immunomodulatory therapy.

In one aspect, disclosed is a method for treating a confirmed or likely COVID-19 positive individual. In this aspect, the method may comprise calculating a MCP-3/IL-8 score, wherein if a high MCP-3/IL-8 score is calculated (as compared to a healthy, non-COVID-19 individual) for said individual, said individual having a high MCP-3/IL-8 score may be administered an immunomodulation therapy. In one aspect, a score of greater than 0.4 is considered a "high score", using the mathematical equation: $\ln[p/(1-p)]=-9.0002+1.1985 \times ihs\,(MCP-3)+1.5457 \times ihs\,(IL-8)$, and indicates that an individual is likely to require ICU care.

Immunomodulation Therapies

In one aspect, applying the methods set forth above, an individual may be administered an immunomodulation therapy. In one aspect, the immunomodulation therapy may be selected from a JAK-inhibitor, an anti-IL-6 (see, e.g., that described in U.S. Pat. No. 8,992,920B2) agent, an anti-IL-8 agent (see, e.g., that described in U.S. Pat. No. 7,622,559B2), an anti-IL-10 agent (see, e.g., that described in U.S. Pat. No. 8,956,607B2), an anti-IL18 agent (see, e.g., that described in US20190031753A1), an anti-M-CSF agent (such as, for example, an antibody according to U.S. Pat. No. 8,142,777B2), an anti-IFN-γ agent (see, e.g., that described in U.S. Pat. No. 8,529,893B2), a complement inhibitor, a corticosteroid. Exemplary corticosteroids include prednisolone, methylprednisolone, triamcinolone, dexamethasone, betamethasone, cortisone or their respective derivatives, such as prednisolone acetate, methylprednisolone acetate, triamcinolone acetate, betamethasone phosphate, and combinations thereof. Further examples with tradenames include, bethamethasone, (Celestone); prednisone (Predni-sone Intensol); prednisolone (Orapred, Prelone); triamcinolone (Aristospan Intra-Articular, Aristospan Intralesional, Kenalog); methylprednisolone (Medrol, Depo-Medrol, Solu-Medrol); dexamethasone (Dexamethasone Intensol, DexPak 10 Day, DexPak 13 Day, DexPak 6 Day), and combinations thereof. In one aspect, administration of the immunomodulation therapy may be repeated every day, or every two days, or every three days, and may be administered in at least one dose, or at least two doses, or at least three doses, or at least four doses, or in certain aspects, more than four doses. A dose may comprise 1 mg or less to about 1,000 mg or more of an active agent provided herein, for example, from about 10, 20, 30, 40, 50, 60, 70, 80, 90, or 100 mg to about 150, 200, 250, 300, 350, 400, 450, 500, 550, 600, 650, 700, 750, 800, or 900 mg. A dosage appropriate to the patient and the number of doses to be administered daily may thus be conveniently selected. In certain embodiments two or more of the therapeutic agents may be incorporated to be administered into a single tablet or other dosage form (e.g., in a combination therapy); however, in other embodiments the therapeutic agents may be provided in separate dosage forms.

In some embodiments, an active agent provided herein may be administered by intravenous, parenteral, or other injection, in the form of a pyrogen-free, parenterally acceptable aqueous solution or oleaginous suspension. Suspensions may be formulated according to methods well known in the art using suitable dispersing or wetting agents and suspending agents. The preparation of acceptable aqueous solutions with suitable pH, isotonicity, stability, and the like, is within the skill in the art. In some embodiments, a pharmaceutical composition for injection may include an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils may be employed conventionally as a solvent or suspending medium. For this purpose, any bland fixed oil may be employed including synthetic mono or diglycerides. In addition, fatty acids such as oleic acid may likewise be used in the formation of injectable preparations. The pharmaceutical compositions may also contain stabilizers, preservatives, buffers, antioxidants, or other additives known to those of skill in the art. The duration of the injection may be adjusted depending upon various factors, and may comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration. In certain aspects, the administration may be carried out over a period of about one week, or about two weeks, or about three weeks, or from about four to about 15 weeks, or longer. In certain aspects, the immunomodulation therapy may be administered weekly. The administration may be carried out via any method as is known in the art, for example, intravenously, subcutaneously, intramuscularly, and/or orally. In one aspect, the administration may be carried out until a desired response or a complete disease response is achieved in the subject.

In one aspect, the immunomodulation therapy may be a JAK kinase inhibitor. In one aspect, the immunomodulation therapy may be an inhibitor of Janus kinase (JAK) 1 and JAK2. Nonlimiting JAK inhibitors may be selected from Ruxolitinib (Incyte), Baricitinib (Incyte), Tofacitinib (Pfizer), INREBIC (Fedratinib) (Celgene/BMS), and combinations thereof. In one aspect, the JAK inhibitor may be ruxolitinib. Ruxolitinib ((3R)-3-cyclopentyl-3-[4-(7H-pyrrolo[2,3-d]pyrimidin-4-yl)pyrazol-1-yl]propanenitrile) is the first FDA approved Janus kinase (JAK) inhibitor and is the only drug currently approved for treatment of myelofibrosis. Ruxolitinib and the synthesis of ruxolitinib are well known in the art, and described in, for example, U.S. Pat. No. 7,598,257 (which describes a process for the preparation of ruxolitinib), WO2016035014A1 (which relates to processes for the preparation of ruxolitinib and ruxolitinib phosphate), and U.S. Pat. No. 8,722,693 (which relates to sustained-release formulations and dosage forms of ruxolitinib, or a pharmaceutically acceptable salt thereof.) The disclosed methods may use any of the ruxolitinib forms or formulations as described in the aforementioned references, and are not limited to such forms or formulations. Dosage of the JAK inhibitor, for example ruxolitinib, may vary. For example, the JAK inhibitor (such as ruxolitinib) may be administered to an individual at a dose of about 10 mg/day, or about 15 mg/day, or about 20 mg/day, or about 25 mg/day, or about 30 mg/day, or about 35 mg/day, or about 40 mg/day, or about 45 mg/day, or about 50 mg/day, or about 55 mg/day, or about 60 mg/day, or about 65 mg/day, or about 70 mg/day, or about 75 mg/day, or about 80 mg/day, or about 85 mg/day, or about 90 mg/day, or from about 10 to about 100 mg/day, or about 25 to about 75 mg per day, or about 30 to 50 mg/day, or from about 100 to about 200 mg/day, or greater than 200 mg/day. The administration may be carried out once a day, twice a day, three times a day, more than four times a day, or continuously administered throughout a day.

In one aspect, the immunomodulation therapy may comprise a complement inhibitor, for a nonlimiting example of which is Eculizumab. Eculizumab is a humanized anti-human C5 monoclonal antibody (Alexion Pharmaceuticals, Inc.), with a human IgG2/IgG4 hybrid constant region, so as to reduce the potential to elicit proinflammatory responses, and is sold under the tradename Soliris®.

In one aspect, the method may further comprise administering an anti-viral therapy (e.g., remdesivir), wherein said anti-viral therapy is administered while a SARS-CoV-2 viral load is detectable in said individual.

The disclosed methods may further employ the administration of a TYK2 inhibitor. An exemplary TYK2 inhibitor includes BMS-986165, available from Celgene/BMS. In yet another aspect, the methods may further employ the administration of a one or both of a corticosteroid and an anti-viral. In a further aspect, the methods may be carried out in the absence of a steroid.

In a further aspect, the disclosed methods may further employ the administration of one or both of an mTOR inhibition (such as rapamycin) and metformin to said individual, before, during, or after administration of said JAK inhibitor. Sirolimus, also known as rapamycin, is a macrolide compound known in the art used to prevent organ transplant rejection and treat a rare lung disease called lymphangioleiomyomatosis. Rapamycin (sirolimus) is believed to have immunosuppressant functions in humans and is useful in preventing the rejection of kidney transplants. Rapamycin is believed to inhibit activation of T cells and B cells by reducing their sensitivity to interleukin-2 (IL-2) through mTOR inhibition. Metformin, marketed under the trade name Glucophage among others, is the first-line medication for the treatment of type 2 diabetes. In a yet further aspect, the method may further comprise administration of an antiviral antibody, and anti-serum, or anti-viral therapy, in combination with any of the aforementioned active agents, or combination thereof. Such administration of compounds may be in succession or at the same time.

The cytokine storm in COVID-19 is believed to be triggered by macrophage activation and release cytokines. It is associated with lysosome activation, phagocytosis. Metformin and rapamycin are known inhibitors for AMPK and mTOR, which inhibit lysosome activation, and may be used in conjunction with the JAK inhibitors disclosed herein. Chloroquinine/Hydrochloroquinine (CQ/HCQ) function at similar steps with much lower activity. Applicant hypothesizes that Metformin and Rapamycin are likely to work better than CQ/HCQ and may be used in conjunction with the JAK inhibitors disclosed herein. Cytokine storm in COVID-19 patients is believed to be triggered by macrophage activation and cause release of cytokines. It is believed to be associated with lysosome activation, and phagocytosis. Without intending to be limited by theory, it is believed that kinase inhibitors such as ruxolitinib, metformin, and rapamycin are much more potent and specific than chloroquinine/hydroxychloroquinine. Because SARS-CoV-2 infection and disease progress very quickly, there is a need for quickly administering effective treatment for severe patients. Thus, in one aspect, administration according to the aforementioned methods may be implemented immediately following a determination that SARS-CoV-2 infection is severe. In other aspects, the administration may occur immediately upon confirmation or suspicion of SARS-CoV-2 infection, particularly in high risk individuals. It is believed that macrophage activation may be controlled through inhibiting AMPK/mTOR pathway (using, for example, metformin/rapamycin). This can be administered before, during or after administration of ruxolitinib. In one aspect, the ruxolitinib is administered following AMPK/mTOR administration.

Complement inhibitor. In certain aspects, the immunomodulatory therapy may comprise a drug or an antibody capable of inhibiting the complement pathway. In one aspect, the antibody may comprise a monoclonal antibody capable of inhibiting the complement pathway. In other aspects, the drug may comprise a humanized monoclonal antibody capable of inhibiting the complement pathway. In certain aspects, the drug may be eculizumab, available from Alexion Pharmaceuticals, and sold under the trade name Soliris.

Kits

Methods employing the above described biomarkers may further employ the use of kits. For example, in one embodiment, provided herein are kits comprising reagents for detecting one or more biomarkers, or the level thereof, wherein the reagents may include antibodies or nucleic acids that detect one or more of the described biomarkers. Reagents may be labelled. In one aspect, the kit may include instructions for detecting the label qualitatively or quantitatively.

In some aspects, the kit may include appropriate buffers, salts and other reagents to facilitate amplification and/or detection reactions (e.g., primers, labels) for determining the level of one or more biomarker, a buffering agent, a preservative, or a protein stabilizing agent. In one embodiment, the kit further comprises an enzyme or a substrate. In one aspect, the detection method used may include PCR, ELISA, RIA, and other similarly recognized methods, and the reagents comprise those appropriate for the particular assay for detection. Methods of detecting the described biomarkers/ cytokines are understood in the art and not limited to any particular assay.

Kits may include one or more reaction vessels that have aliquots of some or all of the reaction components. Aliquots can be in liquid or dried form. Reaction vessels can include sample processing cartridges or other vessels that allow for the containment, processing and/or amplification of samples in the same vessel. The kits may comprise a plurality of detection agents that hybridize or bind to one or more biomarkers described herein. Detection agents may be immobilized on an array as described herein. In one aspect, the results obtained are compared to a standard, which may comprise a series of standards, which may be used in the kits for quantification of differential levels of the biomarker or differential expression. In one aspect, the standard may comprise any embodiment listed herein, and in another embodiment, will be suitable for a particular application of the kit. In one aspect, the standard comprises antibodies for detecting a standard biomarker. In one aspect, the standard comprises nucleic acids when the kit is used for the determination of nucleic acid profile, or in another aspect the standard is a protein when the kit is used for the determination of expressed protein profile. The kit may be adapted for high-throughput screening, and comprise a microarray, and may include a positive and negative control, wherein said standards can be assayed and compared to the test sample.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

Example 1

In this study, Applicant conducted a multiplex screen for 48 cytokines in a total of 242 COVID-19 patients. Applicant aimed to define the determinant cytokines driving the ICU admission and develop clinically relevant risk strata for COVID-19 patients using identified cytokines.

Methods

Clinical Specimens and Study Design.

This study population including the training, internal validation test and external validation sets consisted of 242 participants with newly diagnosed COVID-19 between Feb. 8, and Feb. 29, 2020 in Tongji Hospital. 181 participants were from the wards managed by Tongji medical team, and randomly assigned (3:1) to the training (n=136) or internal validation test (n=45) sets using a random number generator. 61 participants of an external validation set were from other medical wards independently managed by national medical teams. Serum samples were prospectively collected within the first 72 h of hospitalization in the general wards (non-ICU) or intensive care units (ICU) according to the study design (Figure S1). Exclusion criteria included: (1) no clinical and chest radiographic data were available; (2) no written informed consent could be obtained. However, written informed consent could be waived if the patient is too unwell to provide it; (3) patients enrolled in remdesivir or other treatment clinical trials. This study was approved by the Medical ethics committee of Tongji Hospital, Tongji Medical College, Huazhong University of Science and Technology, Wuhan, China. Written informed consent was obtained from all patients, and waived if the patient too unwell to provide it in light of emerging infectious diseases. Patients' data were recorded in an electronic data capture system (EDCS), including demographics, medical history, oximetric assessment, swabs monitoring, radiography and clinical outcomes. Medical data from electronic health records were extracted using a standardized data collection form. Each medical ward used standardized guidance to minimize variability in the diagnosis and treatments. This study also included cryopreserved serum samples collected from five patients with grade 3-4 cytokines release syndrome (CRS) due to anti-BCMA chimeric antigen receptor (CAR) T cell therapy and 22 healthy donors. In addition, 10 patients with a positive bacterial blood culture were included in this study, whose cytokine levels had been measured by electroluminescence in our previous study, but the data were unpublished elsewhere.

Sample Collection.

Blood samples were collected and immediately transferred to 4° C. refrigerator and processed within 24 hours. Serum samples were collected using a serum separator tube (SST) and allow samples to clot for 30 minutes at room temperature before centrifuging for 15 minutes at 1000×g. Serum samples were analyzed immediately or stored at ≤−80° C. until assay. Repeated freeze-thaw cycles was avoided.

Cytokines Measurement.

The levels of serum cytokines were determined by Bio-Plex Pro Human Cytokines 48-Plex Screening assay (Bio-Rad Life Sciences, Hercules, Calif., USA) using a Luminex FlEXMAP 3D system (Luminex, Austin, Tex., USA) according to the manufacturer's protocols. The 48-Plex Screening panel: Basic FGF, CTACK, eotaxin, G-CSF, GM-CSF, GRO-α, HGF, ICAM-1, IFN-α2, IFN-γ, IL-1α, IL-1rα, IL-2, IL-2Rα, IL-3, IL-4, IL-5, IL-6, IL-7, IL-8, IL-9, IL-10, IL-12, IL-13, IL-15, IL-16, IL-17A, IL-18, IP-10, LIF, MCP-1, MCP-3, M-CSF, MIF, MIG, MIP-1α, MIP-1β, β-NGF, PDGF-BB, RANTES, SCF, SCGF-β, SDF-1α, TNF-α, TNF-β, TRAIL, VCAM-1, VEGF-A. Data was analyzed using Bio-Plex Manager 6.2 software (Bio-Rad Life Sciences, Hercules, Calif., USA). Undetected values were inputted with a random value between 0 and the limit of detection (LOD) to avoid the artificial reduction of the standard deviation. In order to stabilize the variability of cytokines, inverse hyperbolic sine transformation were employed before statistical modeling.

Scoring CT Images.

Non-contrast enhanced chest CT scans were performed weekly, and if necessary, additional scans were also permitted. A semi-quantitative scoring system was used to estimate the lung involvement according to previous study. Each of the 5 pulmonary lobes was visually scored from 0 to 5. The total score was the sum of these 5 lobes scores, ranging from 0 to 25. For each patient, the CT manifestation with the highest score was defined as the CT peak score and put into further analysis. All CT images of 181 patients in our cohort were reviewed and scored independently by 2 radiologists who were blinded to the clinical features, and final scores were determined by consensus.

Mean Oxygen Score.

Data on patients' changes in oxygen-support requirements were assessed daily from the enrollment to discharge on the seven-category ordinal scale. Patients below score 3 were defined as no need of oxygen. For each patient, the mean oxygen score in oxygen-support requirements was calculated by the formula: mean oxygen score=(score as judged by the seven-category ordinal scale×days at this score+every varied score as judged by the seven-category ordinal scale×days at this score)÷total days of oxygen therapy.

Viral Clearance Time and Peak D-D Dimer Level.

The virus clearance time was defined as the time from enrollment to the first day of two consecutive negative RT-PCR assay on nasopharyngeal swab by at least 24 h apart. The level of D-D dimer in each patient was assessed weekly from the enrollment to discharge. For each patient, the highest level of D-D dimer was defined as the peak D-D dimer level and put into further analysis.

Determination of SARS-CoV-2-Specific IgG.

The SARS-CoV-2-specific IgG were detected by paramagnetic particle chemiluminescent immunoassay (CLIA) using iFlash-SARS-CoV-2 IgM/IgG assay kit and iFlash Immunoassay Analyzer (Shenzhen YHLO Biotech CO., LTD, China).

Statistical Analysis

Two feature selection techniques, least absolute shrinkage and selection operator (lasso) and random forests were simultaneously employed to identify the most important cytokines in distinguishing ICU from non-ICU patients amongst correlated potential predictors from the training set alone. To avoid inconsistent in terms of variable selection in the lasso modeling process, bootstrap ranking procedure were used, in which 1000 bootstrap samplings were carried out and lasso estimates matrix representing variable ranking according to importance was generated, and an external intersection operation was conducted to extract an optimal set of predictors and obtain the robust selected predictors. The penalty parameter λ for lasso was chosen using 10-fold cross-validation in this process. In random forest modeling process, number of decision trees in the forest was set as 2500 and the importance for each cytokine was calculated using the decrease in node impurity weighted by the probability of reaching that node. The node probability can be calculated by the number of samples that reach the node, divided by the total number of samples. The feature importance were then normalized to a value between 0 and 1 by dividing by the sum of all feature importance values and the higher the value the more important the cytokine is. Finally, a union set cytokines were formulated based on the top 10 cytokines selected by either lasso or random forest method. These selected cytokines were entered in a logistic regression model with ICU/non-ICU as the dependent variable and a final model was developed using stepwise method to identify to cytokines significantly associated with ICU admission in the training set. In the resulting algorithm, every cytokine was assigned a weight computed by the model that best fit the data of the training set alone. The sum of these weighted concentrations led to a predicted probability for each individual patient.

Applicant calculated the misclassification error and the area under the receiver operating characteristic curve (AUC) for the internal test data as measures of the predictive performance of the fitted models. Youden index was calculated according to the receiver operating characteristic (ROC) curve to help to define the appropriate cut-off value. All the analyses were performed using the statistical R version 3.6.3 (www.r-project.org) and Python 3.7. The Univariate analysis were assessed with $\chi^2$ test of association for categorical values and U test for continuous values. Correlation between immune scores and clinical characteristics were estimated by Spearman correlation.

Results

Patient Characteristics

A total of 242 patients with COVID-19 treated in non-ICU and ICU wards and assigned into training (n=136), internal validation test (n=45) and external validation test (n=61) sets. The demographic and clinical characteristics of the patients are summarized in Table 1. While the median time from illness onset to enrollment among all three sets was similar, the external test validation set differed significantly from the training and internal test sets in their overall distributions of age, gender, comorbidities, ICU care, treatments and clinical outcomes. Patients in external test set were older than those in training set and internal test set. Patients in the external test set have higher proportion of male, comorbidities than those in the training and internal validation test sets. Patients in the external validation test set had higher proportion of ICU care at enrollment (45.9% versus 10.3% versus 11.1%) than those in training and internal validation test sets, and correspondingly, they had more intensive supportive treatments and more likely to receive non-invasive or invasive mechanical ventilation respiratory support. Patients in the external validation test set had higher mortality than those in training and internal validation test sets. ICU patients in all sets had extremely high mortality. As of April, 22, while most of non-ICU patients in all three sets (99.2% in the training set, 97.5% in the internal validation test set and 100.0% in the external validation test set) had been discharged alive, most of ICU patients in all three sets, 13 patients (86.7%) in the training set, 6 patients (100.0%) in the internal validation test set and 22 patients (78.6%) in the external validation test set, had died in ICU including two transferred from non-ICU wards due to clinical deterioration during the study.

TABLE 1

Demographic and Clinical Characteristics of the Patients.

| Characteristics | Training Set (n = 136) | Internal Test Set (n = 45) | External test Set (n = 61) | p value[a] | p value[b] |
|---|---|---|---|---|---|
| Age, median (IQR), y | 58 (39-68) | 62 (54-69) | 64 (55-70) | 0.0034 | 0.5718 |
| Sex | | | | | |
| Male, No. (%) | 65 (47.8) | 21 (46.7) | 40 (65.6) | 0.0302 | 0.0730 |
| Comorbidity, No. (%) | 68 (50.0) | 26 (57.8) | 41 (67.2) | 0.0300 | 0.4153 |
| Hypertension | 34 (25.0) | 18 (40.0) | 23 (37.7) | | |
| Diabetes | 23 (16.9)* | 10 (22.2) | 17 (27.9) | | |
| Coronary artery heart disease | 13 (9.6) * | 3 (6.7) | 8 (13.1) | | |
| Cancer | 7 (5.1) | 2 (4.4) * | 2 (3.3) | | |
| COPD | 3 (2.2) | 0 | 2 (3.3) | | |
| Time from illness onset to enrollment, median (IQR), day | 21 (13-25) | 19 (14-25) | 21 (16-26) | 0.4308 | 0.3126 |
| ICU care at enrollment, No. (%) | 14 (10.3) | 5 (11.1) | 28 (45.9) | <0.0001 | 0.0010 |
| Treatment during study period, No. (%) | | | | | |
| Antibiotics | 105 (77.2) | 34 (75.6) | 44 (72.1) | 0.4752 | 0.8243 |
| Antivirals[#] | 119 (87.5) | 40 (88.9) | 54 (88.5) | 0.3032 | >0.9999 |
| Corticosteroids | 67 (49.3) | 25 (55.6) | 38 (62.3) | 0.1221 | 0.5504 |
| Intravenous Immunoglobin | 28 (20.6) | 7 (15.6) | 20 (32.8) | 0.0742 | 0.0700 |
| ECMO | 2 (1.5) | 1 (2.2) * | 3 (4.9) | 0.1734 | 0.6353 * |
| Renal replacement therapy | 6 (4.4) | 3 (6.7) * | 13 (21.3) | 0.0005 | 0.0535 * |
| Highest level of respiratory support, No.(%) | 21 (15.4) | 7 (15.6) * | 33 (54.1) | <0.0001 | <0.0001 |
| High-flow nasal cannula oxygen therapy | 1 (0.7) | 1 (2.2) | 4 (6.6) | | |
| Non-invasive mechanical ventilation | 5 (3.7) | 1 (2.2) * | 4 (6.6) | | |
| Invasive mechanical ventilation | 15 (11.0) | 5 (11.1) | 25 (41.0) | | |
| Outcomes at data cutoff, No. (%) | | | | <0.0001 | 0.0050 |
| Discharged alive | 122 (89.7) | 39 (86.7) | 36 (59.0) | | |
| Died | 13 (9.6) | 6 (13.3) | 22 (36.1) | | |
| Hospitalization | 1 (0.7) | 0 | 3 (4.9) | | |
| Outcomes of non-ICU patients, No. | 122 | 40 | 33 | >0.9999 | >0.9999 |
| Discharged from hospital, No. (%) | 121 (99.2) | 39 (97.5) | 33 (100) | | |
| Transfer to ICU, No. (%) | 1 (0.8) | 1 (2.5) | 0 | | |
| Outcomes of ICU patient†, No. | 15 | 6 | 28 | >0.9999 | >0.9999 |
| Discharge alive, No. (%) | 1 (6.7) | 0 | 3 (10.7) | | |
| Died in ICU, No. (%) | 13 (86.7) | 6 (100) | 22 (78.6) | | |
| Still in ICU, No. (%) | 1 (6.7) | 0 | 3 (10.7) | | |

COPD denotes chronic obstructive pulmonary disease; ICU intensive care unit; ECMO Extracorporeal Membrane Oxygenation;
[a]p-value for comparison of training set to external test set;
[b]p-value for comparison of internal test to external test set;
[#]Abidol hydrochloride and/or Oseltamivir;
†Two of non-ICU patients at enrollment (one in the training set and the other one in the internal test set) were transferred to ICU because of clinical deterioration, and eventually died in ICU.

Cytokine Profiling in Patients with COVID-19

Applicant initially conducted a multiplex screen for 48 cytokines in a total of 181 COVID-19 patients including training and internal validation test sets. The concentration of each of 48 cytokines was compared between COVID-19 patients and healthy donors to outline the overall host inflammatory cytokine response to defend against SARS-CoV-2 infection. The levels of 14 cytokines, including MCP1, MIP-1α, MIP-1β, IL-1Rα, IL-2Rα, IL-5, IL-15, IL-18, LIF, M-CSF, TNF-β, HGF, SCF and SCGF-β were significantly increased in COVID-19 patients compared to those in healthy donors. Interestingly, the levels of 4 pro-inflammatory cytokines IL-1α, IL-7, IL-12 (p70) and IL-17A were significantly decreased in COVID-19 patients compared to healthy controls. The cytokine profile was dramatically different between ICU and non-ICU patients. The levels of 17 inflammatory cytokines in ICU patients, including IL-8, IP-10, MCP-1, MCP-3, MIP-1α, IL-1α, IL-1Rα, IL-6, IL-10, IL-16, IL-17A, IL-18, IFN-γ, M-CSF, β-NGF, HGF, and SCF were significantly increased in ICU patients. On the other hand, the levels of 3 cytokines RANTES, GM-CSF and TRAIL were significantly decreased in ICU compared to those in non-ICU patients. The cytokine profiles in ICU patients were further compared with those in patients with active bacterial septicemia and patients with severe (grade 3-4) cytokine release syndrome (CRS) secondary to anti-BCMA chimeric antigen receptor (CAR) T cell therapy.

The cytokine levels were adjusted to average baseline level of healthy donors and log 2-transformed, and subjected to unsupervised clustering analysis. Distinct signatures of cytokine storm was found in COVID-19 patients compared to CRS and bacterial sepsis, indicative of the portraits of cytokine storm of ICU patients did not exactly match those in other disease entities. In general, the cytokine responses to bacterial septicemia and CAR-T were much broader than to SARS-CoV-2 infection. Interestingly, cytokine response to SARS-CoV-2 infection was featured by low levels of a type I interferon (IFNα2) juxtaposed to elevated chemokines and high expression of many cytokines such as IFNγ, IL-6 in contrast to those in CRS and bacterial sepsis. Unexpectedly, levels of TNFα, IL-1β, IL-2, IL-12 and GM-CSF, some of which had been previously proposed as therapeutic targets for COVID-19 immunomodulation, did not significantly elevated. While profound elevated level of IL-6 were consistently observed in COVID-19, bacterial sepsis as well as CAR-T CRS, increased MCP-3 was only featured in patients with COVID-19 or CAR-T CRS but not in bacterial sepsis. Thus, Applicant unexpectedly found that existing proposal for therapies—including anti-TNFα, IL-1β, IL-2, IL-12 or anti-GM-CSF therapies—may not be efficacious against cytokine response in COVID-19 patients.

Importance Ranking of Cytokines to Distinguish ICU from Non-ICU Patients

Figure 2:
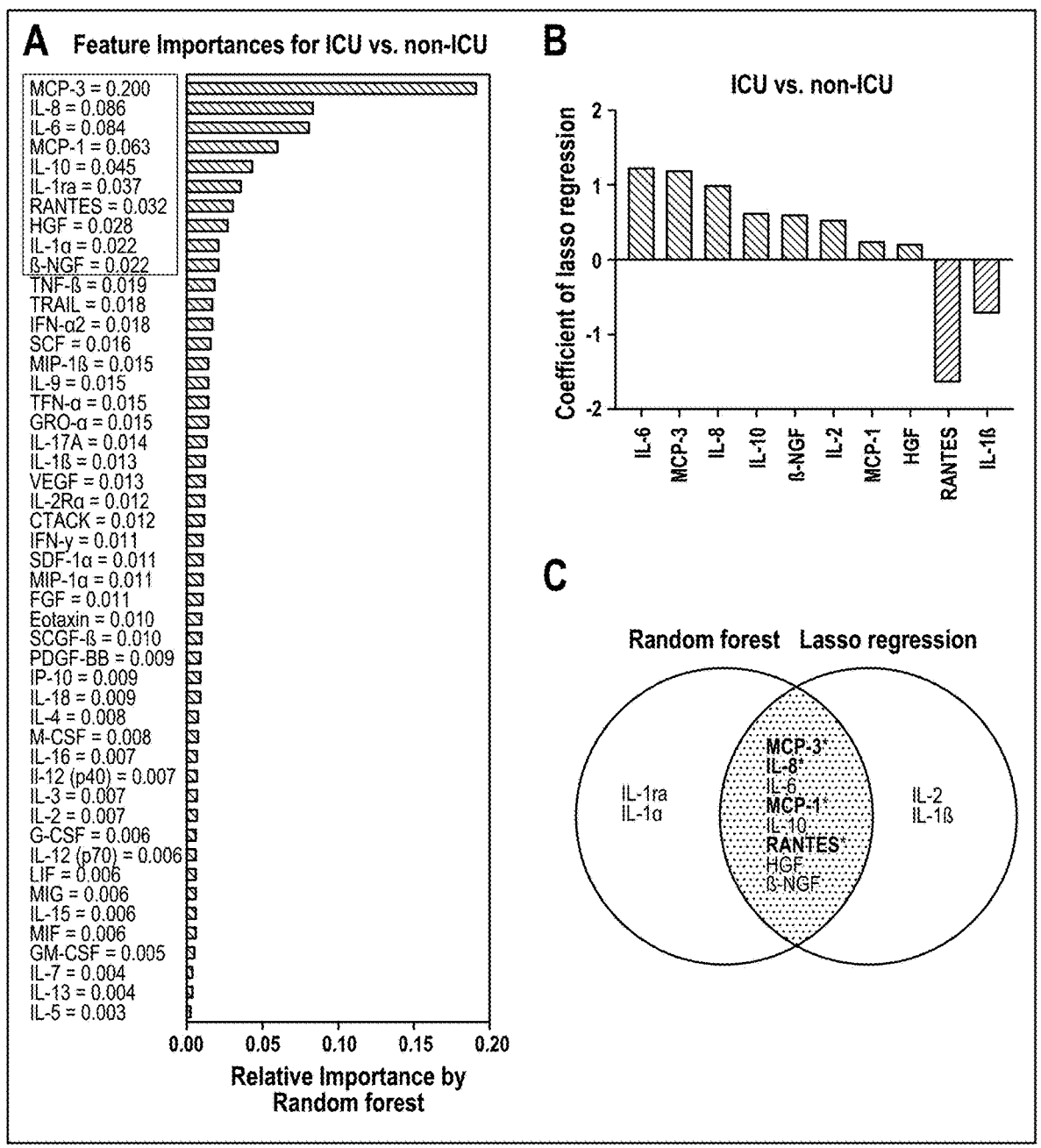
FIG. 2. Cytokine importance ranking by random forest and lasso regression. (A) The most significant predictors for ICU admission identified by random forest. Relative variable importance is illustrated. (B) Lasso regression identified 10 analytes contributed to distinguish ICU from non-ICU patients. The coefficient is shown. Bars represent cytokines positively and negatively contributed to the lasso regression model. (C) Venn results of random forest and lasso modeling. *, chemokines.

To identify the most important cytokines correlated to the risk for ICU admission, 181 patients were randomly assigned (3:1) using a random number generator into training (n=136) and internal validation test (n=45) sets. In the training set, random forest model and least absolute shrinkage and selection operator (lasso) regression were simultaneously employed for feature selection. By utilizing random forest, Applicant ranked ordered the importance of 48 cytokines based on their ability to discriminate between ICU and non-ICU patients. As shown in FIG. 2A, MCP-3 ranked the most important cytokine, followed by IL-8, IL-6, MCP-1, IL-10, IL-1rα, RANTES, HGF, IL-1α and β-NGF. The bootstrap ranking lasso regression also identified a 10-cytokine set for discriminating between ICU and non-ICU patients, including IL-6, MCP-3, IL-8, IL-10, β-NGF, IL-2, MCP-1, HGF, RANTES and IL-1β (FIG. 2B). Both of the two models identified uniformly MCP-3, IL-8, IL-6, MCP-1, RANTES, β-NGF, IL-10 and HGF as the most important cytokines, which highlights the important role of chemokines in distinguishing ICU from non-ICU patients (FIG. 2C). As can be seen in FIG. 2B/2C, MCP-3, IL-8, IL-6, MCP-1, β-NGF, IL-10 and HGF go up, but RANTES goes down in ICU patients.

Developing and Validating a Cytokine-Based Algorithm to Compute a Probability of ICU Admission To develop a cytokine-based algorithm to compute a probability of ICU admission, a union set of top ten cytokines selected by random forest model and lasso regression including MCP-3, IL-8, IL-6, MCP-1, RANTES, β-NGF, IL-10, HGF, IL-1rα, IL-1α, IL-16 and IL-2 were entered in a logistic regression model with ICU/non-ICU care as the dependent variable. In order to build a parsimonious model, Applicant used forward stepwise variable selection approach to select the final predictors. The final model identified combination of MCP-3 and IL-8 was the strongest predictor of ICU admission, with P-value≤0.05. Furthermore, the coefficients calculated by the logistic regression model enable a weight assigned to each cytokine and then a predicted probability of ICU admission for each individual patient could be obtained by summing up these weighted concentrations. The resulting MCP-3 and IL-8 algorithm was then used to compute the probability of ICU admission by a mathematical equation: $\ln[p/(1-p)] = -9.0002 + 1.1985 \times \text{ihs (MCP-3)} + 1.5457 \times \text{ihs (IL-8)}$.

Figure 3:
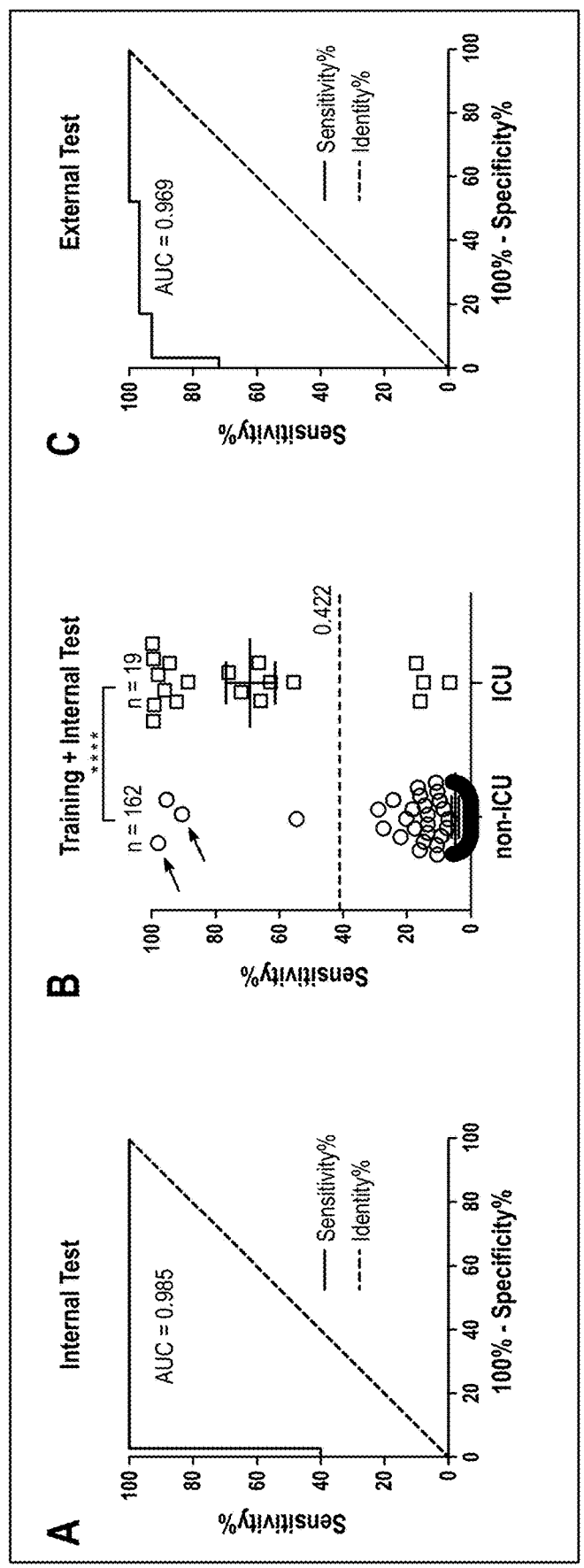
FIG. 3. MCP-3/IL-8 immune score shows good performance in reflecting COVID-19 disease risk. (A) Receiver operating characteristic (ROC) curve evaluation of the performance for immune scores to diagnose the COVID-19 patients needing ICU admission in the internal test set. The area under ROC curve (AUC) is 0.985 which shows a high diagnostic ability. (B) Comparison of immune scores in non-ICU and ICU patients of training and internal test sets. Arrows indicate patients who were transferred to ICU wards during follow up. r, spearman's correlation coefficient. (C) ROC curve evaluation of the performance for immune scores to diagnose the COVID-19 patients needing ICU admission in the external test set. (D) Comparison of immune scores in non-ICU and ICU patients from external test sets. (E-H) Spearman correlation between MCP-3/IL-8 immune score and peak CT value, mean oxygen score, peak D-Dimer level, ratio of IFN-α2/IFN-γ concentration. (I) Different outcomes (dead and alive) in ICU patients show significant difference in MCP-3/IL-8 immune scores. , P<0.01; **, P<0.0001. U-test is used.
Figure 3:
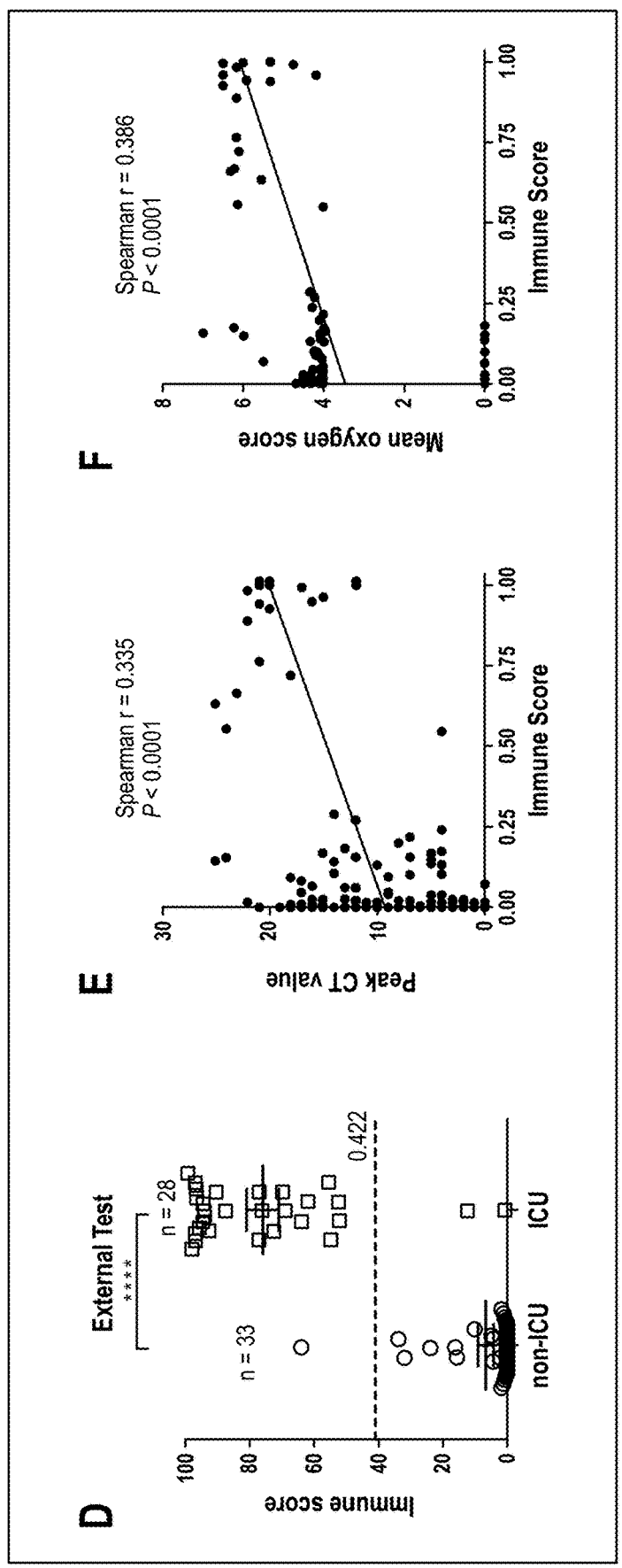
Figure 3:
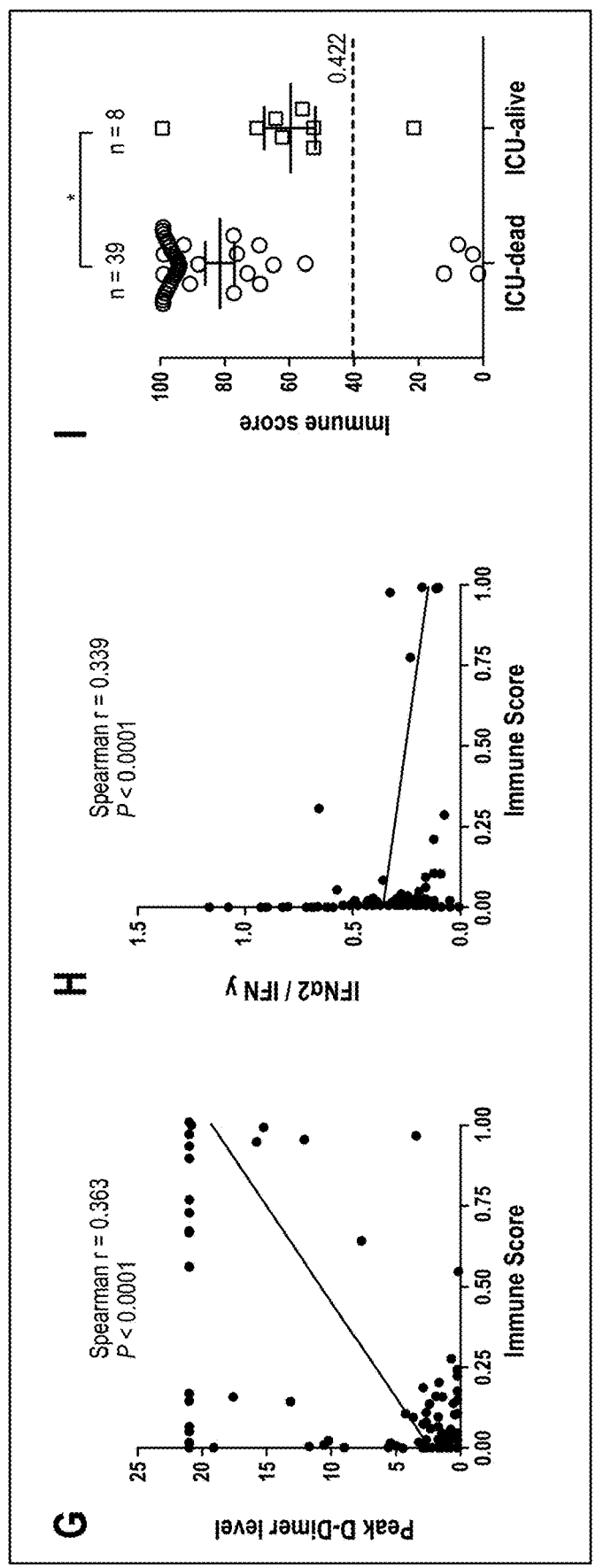
Figure 4:
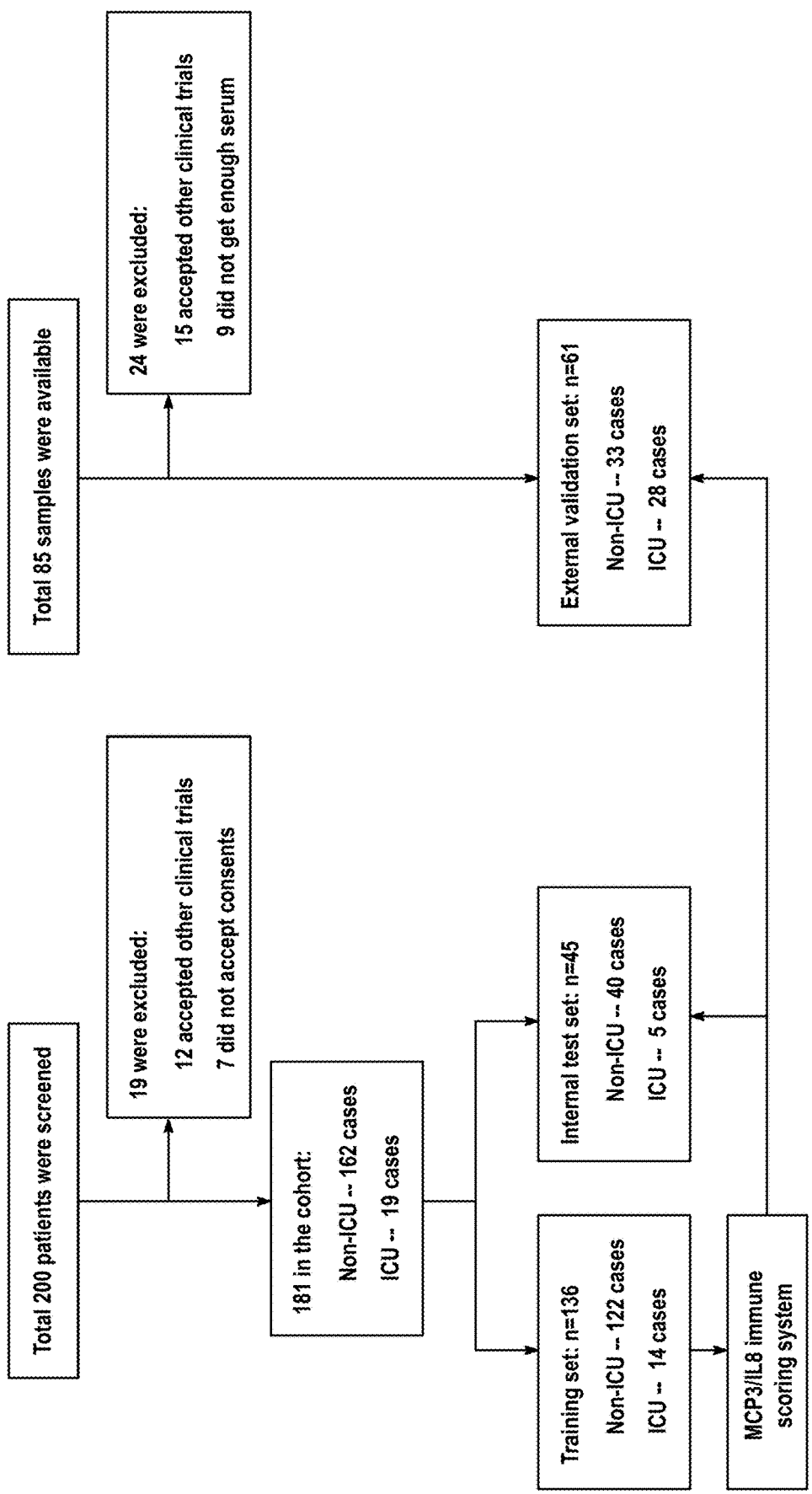
FIG. 4. Flow chart of the study

The performance of the MCP-3/IL-8 algorithm was evaluated in internal validation test set by ROC analysis and the prediction cut off was set at 0.422 by maximizing the Youden's index. The patients with predicted value greater than 0.422 were defined as with high MCP-3/IL-8 score (FIG. 3A). At this cut off, the sensitivity and specificity were 100% (5/5) and 97.5% (39/40) in the internal validation test set, respectively. In addition, the positive predictive value and negative predictive value were 83.3% (5/6) and 100% (39/39) in the internal validation test set. the positive predictive value and negative predictive value were calculated, which were 78.9% (15/19, ICU admission) and 97.5% (158/162, non-ICU admission). Of four non-ICU patients identified with high MCP-3/IL-8 score at enrollment, 2 of them were eventually transferred to ICU and died due to the progressive disease (FIG. 3B).

The MCP-3/IL-8 algorithm was further validated in the external validation test set. The external validation test set included 28 (45.9%) ICU and 33 (50.1%) non-ICU patients with significantly different baseline demographic and clinical characteristics. ROC curve built from the external test set was shown in FIG. 3C. For this independent patients set, the sensitivity and specificity were 92.86% and 97.14% using the same cut off of 0.422. The immune scores in ICU patients were significantly higher than that of non-ICU patients (FIG. 3D).

MCP-3/IL-8 Scores Well Correlated with Clinical Manifestations

Figure 5:
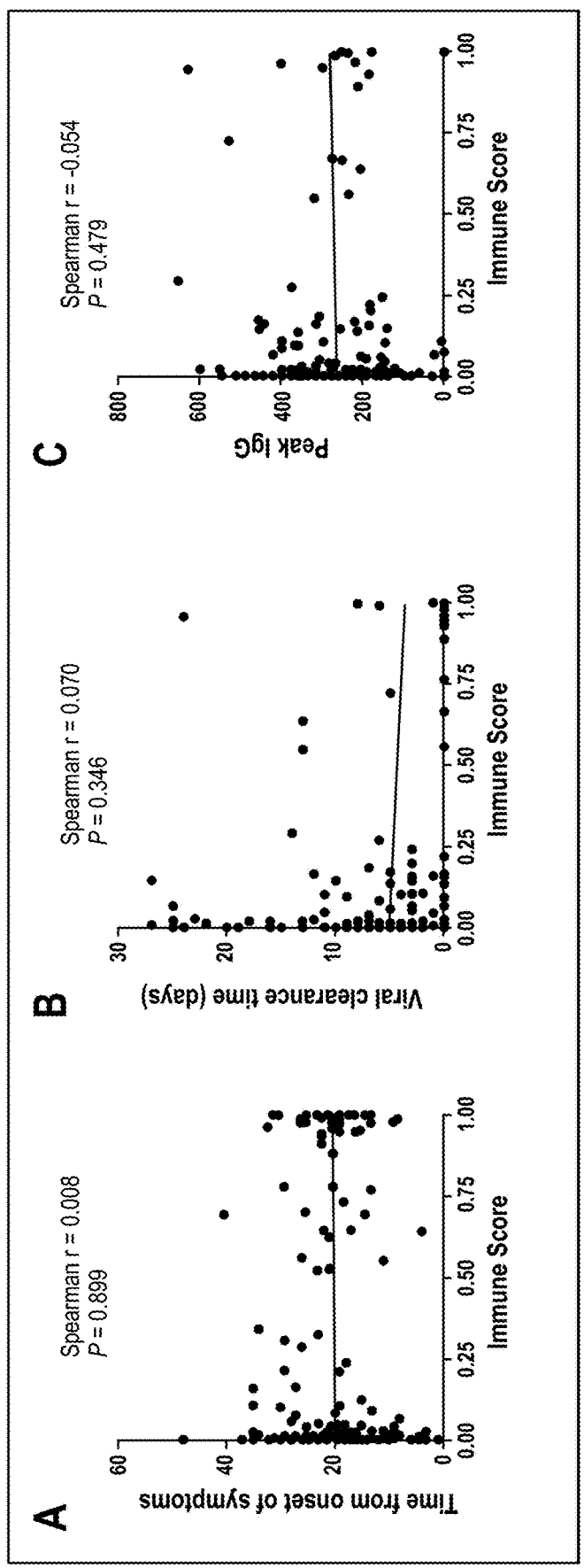
FIG. 5. Correlation between MCP-3/IL-8 immune score and viral clearance time, peak IgG levels and time from onset symptoms. r, spearman's correlation coefficient.
Figure 6:
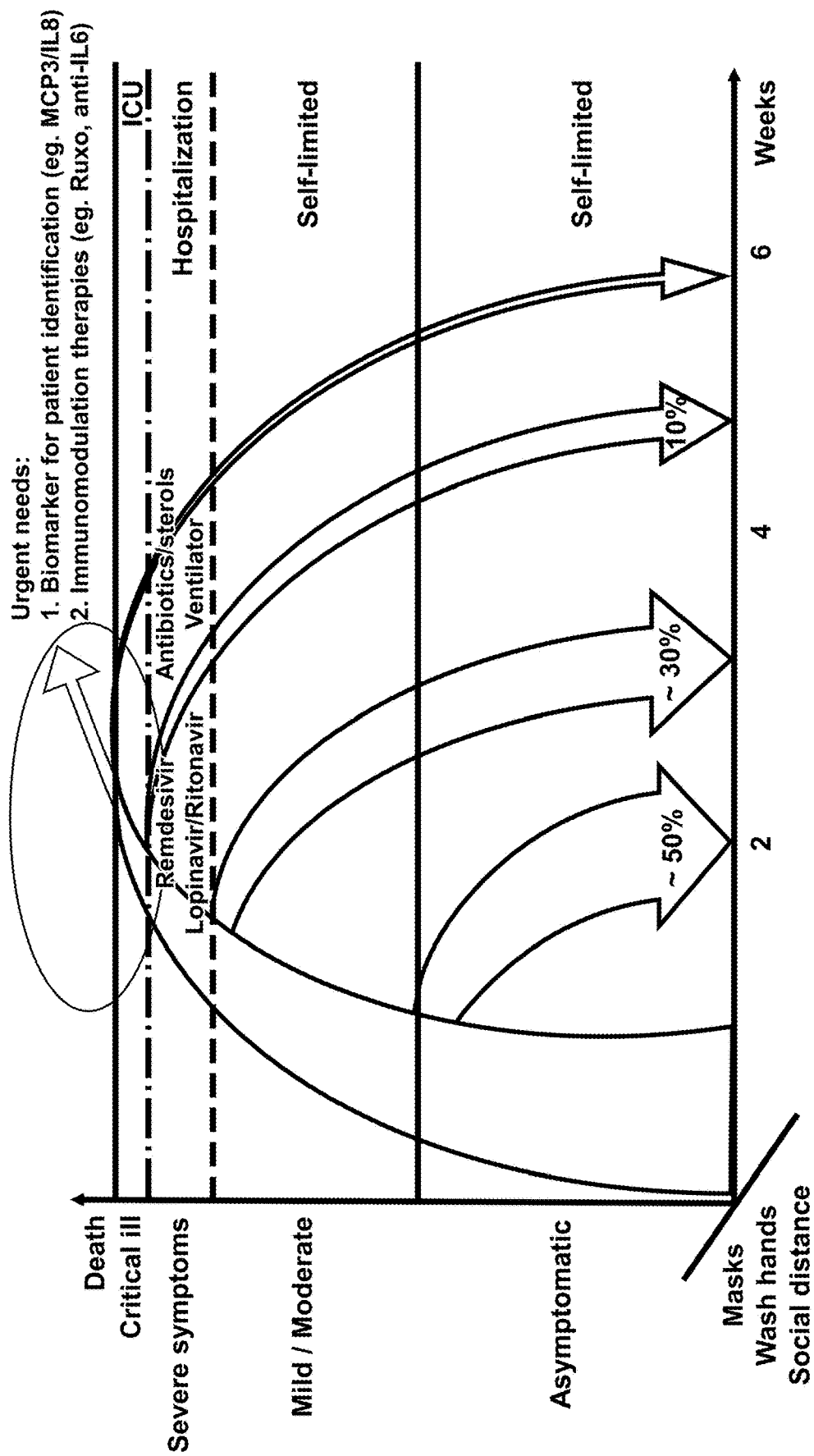
FIG. 6. depicts categories of cases of individuals infected with SARS-CoV-2 (Asymptomatic ("Group 1"), Mild/Moderate ("Group 2"), Severe Symptoms ("Group 3"), and Death/Critically ill ("Group 4")), and the typical hospitalization status for each group (self-limited, hospitalization, and ICU).
Figure 7:
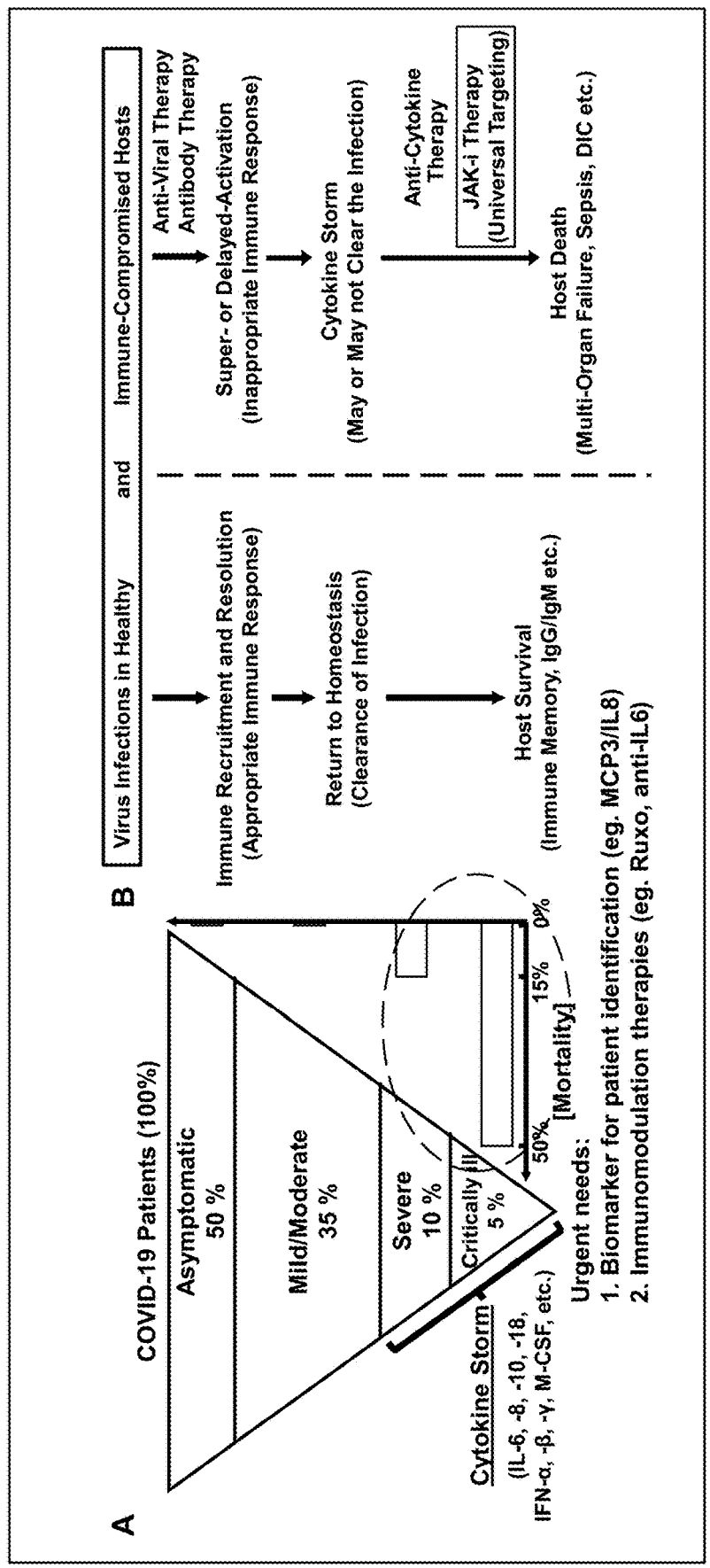
FIG. 7. depicts COVID-19 patients and mortality among Asymptomatic ("Group 1"), Mild/Moderate ("Group 2"), Severe Symptoms ("Group 3"), and Death/Critically ill ("Group 4") patients (A) and a schematic of virus infection in healthy and immune-compromised hosts (B).

To further explore the correlation of cytokine profile with clinical manifestations, each of 181 patients was scored by MCP-3/IL-8 algorithm for the severity of their cytokine storm. First of all, MCP-3/IL-8 scores in 181 COVID-19 patients were analyzed for their correlation with the enrollment time to rule out the possible bias that different scores might be the unspecific results of cytokine determination at varied time to illness onset. However, the difference in MCP-3/IL-8 scores were unlikely brought about by the disparity in enrollment time since there was no correlation between scores and enrollment time (FIG. 5, A). The score of cytokine storm in each individual patient was further analyzed by spearman correlation tests for their correlation with mean oxygen score, CT peak score, peak level of D-Dimer and IFNα2/IFNγ. These clinical parameters were chosen because oxygen demand and CT manifestation were the strongest factors to define the illness severity of COVID-19, and level of D-Dimer was a well-known prognostic factor linked to inferior outcome. The ratio of IFNα2/IFNγ was chosen to be explored based on an inspiring finding recently published in Cell (DOI: 10.1016/j.cell.2020.04.026, Imbalanced host response to SARS-CoV-2 drives development of COVID-19, Blanco-Melo et al.). In that study, cytokine response to SARS-CoV-2 infection is defined by low levels of Type I/III interferons juxtaposed to elevated chemokines and high expression of cytokines, which was proposed as the driving feature of COVID-19 and speculated to associate with the high lethality in the older populations. Applicant therefore employed IFNα2 production to represent the innate antiviral defenses and IFNγ as the surrogate cytokine of the systemic inflammatory response, and the ratio of IFNα2/IFNγ as a surrogate marker reflecting the immune imbalance in individual patients. The MCP-3/IL-8 scores were positively correlated with mean oxygen score, CT peak score and peak level of D-Dimer, indicative of the clinical deterioration in COVID-19, at least in part, were a common consequence of an enhanced cytokine storm (FIG. 3E-G). Strikingly, the MCP-3/IL-8 scores showed negative correlation with the ratio of IFNα2/IFNγ, indicative of the severity of cytokine storm in COVID-19 was indeed linked to host immune imbalance (FIG. 3H). Importantly, the patients died in ICU had significantly higher MCP-3/IL-8 scores than ICU-alive patients (FIG. 3I). Finally, to learn whether the severity of cytokine storm influenced the viral clearance time and generation of anti-SAS-COVID-2 antibodies, the score of cytokine storm in each of 181 individual patient was analyzed by spearman correlation tests for their correlation with the viral clearance time and peak levels of anti-SAS-COVID-2 IgG. As depicted in FIG S2B-C, there were no correlation between MCP-3/IL-8 scores and the viral clearance time or peak levels of anti-SAS-COVID-2 IgG. It should be noteworthy that high MCP-3/IL-8 score could be found in a number of COVID-19 cases with complete viral clearance at the time of enrollment (FIG S2B), implying that severe inflammatory response to SARS-CoV-2 could last beyond the clearance of the virus.

Risk Factors of Patients with High MCP-3/IL-8 Scores.

A total of 242 enrolled patients were dichotomized into low-scoring and high-scoring subgroups according to the cut off (0.422) of MCP-3/IL-8 score. Subgroup with high MCP-3/IL-8 score was with the extremely higher probability of ICU admission and mortality. To identify the risk factors for patients with high MCP-3/IL-8 score, the demographic/clinical characteristics, enrollment time, treatments and the ratio of IFN-α2/IFN-γ were compared between low-scoring and high-scoring subgroups by an Univariate analysis. Older age, male and lower ratio of IFN-α2/IFN-γ were found to be significantly associated with high-scoring subgroup. On the other hand, time from illness to enrollment and comorbidities did not significantly different between the two subgroups, although comorbidities of hypertension, diabetes, coronary artery heart disease and COPD were numerically high in high-scoring subgroup. Much more frequent use of treatments of corticosteroid, ECMO and renal replacement therapy in high-scoring subgroup might mirror higher morbidity rate of ARDS or multiple organ failure in this subgroup, and also implying these treatments might not interfere the computation of MCP-3/IL-8 algorithm.

TABLE 2

Comparison of cytokines in different groups of patients.

| Analyte | Healthy (n = 22) mean (s.e.m.) | Total COVID-19 (n = 181) mean (s.e.m.) | Non-ICU (162) mean (s.e.m.) | ICU (n = 19) mean (s.e.m.) | Total COVID-19 versus Healthy P value[a,b] | ICU versus non-ICU P value[a,b] |
|---|---|---|---|---|---|---|
| Chemokine | | | | | | |
| CTACK | 585.73 (37.70) | 1343.38 (101.43) | 1418.97 (110.45) | 698.94 (155.27) | 0.2976 | 0.207 |
| Eotaxin | 73.77 (4.87) | 140.78 (13.03) | 146.65 (14.43) | 90.76 (11.51) | 0.3830 | 0.767 |
| GRO-α | 828.68 (9.86) | 1510.58 (102.38) | 1595.60 (111.21) | 785.64 (150.34) | 0.4963 | 0.076 |
| IL-8 | 6.21 (0.84) | 29.43 (7.25) | 12.41 (1.50) | 174.55 (59.41) | 0.8476 | <0.0001* |
| IP-10 | 472.99 (38.72) | 1629.05 (411.94) | 1594.21 (456.87) | 1926.10 (491.46) | 0.3872 | 0.008* |
| MCP-1 | 34.38 (2.24) | 168.46 (28.30) | 110.52 (19.48) | 662.48 (179.52) | 0.0241* | <0.0001* |
| MCP-3 | 0.16 (0.01) | 1.67 (0.43) | 0.89 (0.40) | 8.29 (1.64) | 0.2380 | <0.0001* |
| MIG | 152.48 (8.19) | 399.62 (53.32) | 386.85 (56.57) | 508.44 (161.36) | 0.4559 | 0.115 |
| MIP-1α | 2.61 (0.16) | 10.40 (0.83) | 9.81 (0.84) | 15.46 (3.22) | 0.0019* | 0.017* |
| MIP-1β | 264.54 (5.52) | 639.29 (43.48) | 672.59 (47.41) | 355.36 (60.66) | 0.0302* | 0.355 |
| RANTES | 16424.37 (1073.75) | 27175.39 (1940.48) | 29250.44 (2092.98) | 9482.93 (2281.74) | 0.9448 | <0.0001† |
| SDF-1α | 845.28 (34.07) | 930.35 (55.57) | 948.30 (60.98) | 777.29 (95.51) | 0.1786 | 0.904 |
| Interleukin | | | | | | |
| IL-1α | 12.78 (1.53) | 8.17 (0.82) | 7.62 (0.86) | 12.91 (2.47) | <0.0001† | 0.002* |
| IL-1β | 4.05 (0.26) | 7.02 (0.60) | 7.39 (0.66) | 3.92 (1.09) | 0.2641 | 0.400 |
| IL-1ra | 157.13 (12.58) | 1246.92 (244.67) | 769.30 (91.79) | 5319.26 (2007.74) | **0.0005 *** | <0.0001* |
| IL-2 | 1.37 (0.18) | 2.16 (0.40) | 2.16 (0.44) | 2.20 (0.52) | 0.4432 | 0.077 |
| IL-2Rα | 60.14 (2.97) | 251.05 (29.41) | 254.65 (32.08) | 220.40 (62.17) | **0.0352 *** | 0.091 |
| IL-3 | 0.06 (0.01) | 0.21 (0.12) | 0.21 (0.14) | 0.15 (0.07) | 0.2060 | 0.760 |
| IL-4 | 7.07 (0.29) | 13.23 (0.91) | 13.88 (0.99) | 7.66 (1.37) | 0.6323 | 0.298 |
| IL-5 | 1.91 (0.30) | 26.01 (18.73) | 27.91 (20.91) | 9.72 (7.04) | **0.0057 *** | 0.650 |
| IL-6 | 1.37 (0.27) | 29.24 (10.17) | 7.85 (1.79) | 211.60 (86.84) | 0.2327 | <0.0001* |
| IL-7 | 14.74 (2.24) | 14.19 (2.28) | 14.27 (2.52) | 13.51 (3.66) | 0.0006 † | 0.073 |
| IL-9 | 391.13 (6.40) | 1006.04 (74.89) | 1071.21 (81.39) | 450.35 (99.48) | 0.3012 | 0.148 |
| IL-10 | 0.70 (0.07) | 5.26 (2.05) | 1.04 (0.12) | 41.25 (17.82) | 0.3573 | **0.002 *** |
| IL-12 (p70) | 3.18 (0.71) | 2.95 (1.52) | 3.14 (1.69) | 1.30 (0.37) | 0.0006† | 0.617 |
| IL-12 (p40) | 8.76 (0.79) | 71.19 (27.08) | 68.60 (29.58) | 93.27 (55.59) | 0.9479 | 0.904 |
| IL-13 | 1.40 (0.23) | 2.45 (0.34) | 2.54 (0.38) | 1.72 (0.30) | 0.7410 | 0.448 |
| IL-15 | 4.40 (0.77) | 66.35 (30.76) | 67.65 (34.15) | 55.29 (34.94) | 0.0087* | 0.767 |
| IL-16 | 61.07 (4.43) | 174.69 (15.04) | 170.44 (16.19) | 210.95 (38.68) | 0.1932 | 0.021* |
| IL-17A | 12.61 (1.29) | 12.15 (1.34) | 12.12 (1.49) | 12.40 (1.82) | 0.0050 † | 0.032* |
| IL-18 | 38.00 (1.94) | 225.67 (33.56) | 196.03 (23.51) | 478.43 (247.35) | 0.0003* | 0.013* |
| LIF | 31.54 (4.84) | 92.52 (9.11) | 95.09 (9.93) | 70.63 (18.98) | 0.0263* | 0.972 |

TABLE 2-continued

Comparison of cytokines in different groups of patients.

| Analyte | Healthy (n = 22) mean (s.e.m.) | Total COVID-19 (n = 181) mean (s.e.m.) | Non-ICU (162) mean (s.e.m.) | ICU (n = 19) mean (s.e.m.) | Total COVID-19 versus Healthy P value[a,b] | ICU versus non-ICU P value[a,b] |
|---|---|---|---|---|---|---|
| Interferon | | | | | | |
| IFN-α2 | 15.94 (0.81) | 21.33 (1.51) | 21.89 (1.63) | 16.51 (3.30) | 0.6907 | 0.614 |
| IFN-γ | 37.82 (3.58) | 111.79 (10.92) | 105.31 (11.61) | 167.06 (29.70) | 0.4747 | 0.002* |
| CSF | | | | | | |
| G-CSF | 5.08 (0.89) | 52.34 (11.39) | 42.93 (9.51) | 132.59 (71.16) | 0.6894 | 0.054 |
| GM-CSF | 0.80 (0.27) | 3.95 (1.52) | 4.23 (1.69) | 1.56 (0.65) | 0.4699 | 0.025 † |
| M-CSF | 10.70 (0.78) | 63.48 (6.99) | 62.44 (7.61) | 72.36 (15.24) | 0.0028* | 0.018* |
| TNF | | | | | | |
| TNF-α | 75.01 (1.77) | 153.80 (10.66) | 161.01 (11.63) | 92.29 (16.18) | 0.6474 | 0.713 |
| TNF-β | 446.59 (8.63) | 1186.65 (86.03) | 1261.38 (93.55) | 549.47 (111.37) | 0.0390* | 0.141 |
| TRAIL | 27.53 (2.03) | 53.41 (5.00) | 57.26 (5.45) | 20.55 (7.10) | 0.5285 | 0.025† |
| Others | | | | | | |
| β-NGF | 0.28 (0.05) | 0.49 (0.09) | 0.42 (0.09) | 1.16 (0.31) | 0.8718 | 0.019* |
| Basic FGF | 70.40 (2.26) | 113.13 (7.84) | 118.50 (8.56) | 67.42 (12.26) | 0.1150 | 0.643 |
| HGF | 304.19 (22.42) | 1096.79 (131.01) | 900.02 (71.09) | 2774.53 (1036.86) | 0.0094* | <0.0001* |
| MIF | 1429.16 (159.67) | 2685.93 (234.31) | 2721.27 (257.39) | 2384.59 (414.90) | 0.8597 | 0.140 |
| PDGF-BB | 2354.93 (209.05) | 5589.81 (543.15) | 5892.54 (594.50) | 3010.89 (858.70) | 0.7121 | 0.090 |
| SCF | 60.55 (2.52) | 183.29 (14.22) | 178.28 (14.98) | 226.00 (45.21) | 0.0072* | 0.032* |
| SCGF-β | 98368.04 (5508.67) | 362846.80 (28718.86) | 380159.52 (31600.72) | 215233.12 (32575.14) | 0.0002* | 0.813 |
| VEGF-A | 2.90 (0.35) | 81.23 (17.73) | 78.87 (19.20) | 101.31 (42.65) | 0.1329 | 0.667 |

[a] Bold text indicates P-values < 0.05.
*cells represent upregulated analytes and
†cells represent downregulated analytes (two-group comparisons).
[b] Mann-Whitney U test with two independent groups (healthy vs. total COVID-19, and non-ICU vs. ICU).

TABLE 3

Comparison of demographic and clinical features between low scoring and high scoring patients. Data are median (range) or n (%); Bold text indicates P-values < 0.05, a Mann-Whitney U test is used for continuous variables and b chi-square test is used for classified variables; COPD denotes chronic obstructive pulmonary disease and ECMO Extracorporeal Membrane Oxygenation.

| Characteristic | low scoring (n = 196) | high scoring (n = 46) | P value |
|---|---|---|---|
| Age, years | 59 (17-87) | 67 (42-86) | <0.0001 [a] |
| Sex, No. (%) | | | 0.0208 [b] |
| Female | 101 (51.5) | 15 (32.6) | |
| Male | 95 (48.5) | 31 (67.4) | |
| Comorbidity, No. (%) | | | |
| Hypertension | 58 (29.6) | 17 (37) | 0.331 [b] |
| Diabetes | 38 (19.4) | 12 (26.1) | 0.3125 [b] |
| Coronary artery heart disease | 17 (8.7) | 7 (15.2) | 0.1814 [b] |
| Cancer | 9 (4.6) | 2 (4.3) | 1.0000 [b] |
| COPD | 3 (1.5) | 2 (4.3) | 0.2415 [b] |
| Time from illness onset to enrollment | 21 (1-48) | 20 (4-32) | 0.7616 [a] |
| Treatment, No. (%) | | | |
| Antivirals | 172 (87.8) | 41 (89.1) | 0.7960 [b] |
| Corticosteroids | 88 (44.9) | 42 (91.3) | <0.0001 [b] |
| ECMO | 1 (0.5) | 5 (10.9) | <0.0001 [b] |
| Renal replacement therapy | 2 (1) | 20 (43.5) | <0.0001 [b] |
| Death (%) | 5 (2.6) | 36 (78.3) | <0.0001 [b] |
| IFN-α2/IFN-γ | 0.33 (0-7.08) | 0.15 (0-0.42) | <0.0001 [a] |

Discussion

In this study, by studying a 48-cytokine profile in a cohort of 242 COVID-19 patients, Applicant obtained several key results with reference to the study objective. In comparison to healthy control, 18 of 48 cytokines varied significantly mirroring a host inflammatory cascade to defend against SARS-CoV-2 infection. The overall cytokine profile in ICU COVID-19 patients was distinct as compared to those in CAR-T recipients and patients with active bacterial septicemia. The cytokines with the strongest prognostic value for ICU admission was MCP-3, followed by IL-8, IL-6, MCP-1, IL-10 IL-1RA, RANTES, HGF and IL-1α in an order of importance. Applicant used the levels of MCP-3 and IL-8 to create an algorithm that computed the probability of ICU admission. The probability of ICU admission and death significantly increased in patients with high MCP-3/IL-8 score. MCP-3/IL-8 score was positively correlated with the severity of the clinical features, severe CT findings and poor lab indexes, indicative of the clinical deterioration in COVID-19, at least in part, were a common consequence of an enhanced cytokine storm. On the other hand, MCP-3/IL-8 score did not correlate with the level of specific anti-SARS-CoV-2 IgG and the time of viral clearance, implying that the enhanced cytokine storm per se did not stand for a better antiviral efficacy. Finally, higher MCP-3/IL-8 score was more likely observed in patients with older age, male, and lower ratio of IFNα2/IFNγ.

Although previous studies had proposed correlations between cytokine storm and inferior clinical outcomes, there was no consensus on what the determinant cytokines are, and how to compute the severity of cytokine storm for an individual patient. The findings presented here address several critical questions. First, this study ranks the driving cytokines in order of importance according to the prognostic value for ICU admission. Meaningfully, the identification of top 5 driving cytokines highlights the fundamental role of overproduced chemokines and IL-6 in driving a fatal outcome, which is consistent with the actual clinical scenarios and findings in biopsy or autopsy studies. Second, the MCP-3/IL-8 score accurately discriminated patients with fatal clinical outcome, and had a positive correlation with deteriorated clinical characteristics, strongly support a key immunopathological role of MCP-3 and IL-8 in driving a clinical deterioration. Using MCP-3/IL-8 score to distinguish high risk COVID-19 patients with fatal outcome is of great clinical significance. Identification of high-risk group may justify the test of appropriate immunomodulatory drugs and facilities patients' selection in clinical trial setting. Third, older age, males were found associated with a higher MCP-3/IL-8 score, which is in line with independent risk factors for severe disease reported previously. Intriguingly, the ratio of IFNα2/IFNγ in Applicant's study were negatively correlated with MCP-3/IL-8 score, which was clinically validated for the first time and might help researchers to further explore the underlying mechanism of why fatal cytokine storm occurred in some but not in the other.

Applicant sought to define the determinant cytokines driving fatal outcome and develop clinically relevant risk strata for COVID-19 patients based on the identified cytokines. Applicant prospectively collected serum from 242 patients with COVID-19 treated in intensive care units (ICU) and non-ICU wards and assigned into training (n=136), internal validation test (n=45) and external Tvalidation test (n=61) sets. A multiplex screen for 48 cytokines in these COVID-19 patients was conducted and analyzed in a training set to identify the determinant cytokines linked to ICU admission. The cytokines with the strongest prognostic value for ICU admission was MCP-3, followed by IL-8, IL-6, MCP-1, and IL-10 in an order of importance. Applicant developed an algorithm using MCP-3/IL-8 that computed the probability of ICU admission in the training set. The algorithm was further evaluated in the internal validation test and external test set. In all three datasets, higher MCP-3/IL-8 score accurately distinguished ICU patients, and had a positive correlation with deteriorated clinical characteristics, severe CT and poor lab indexes. Older age, male and lower ratio of IFNα2/IFNγ were found associated with a higher MCP-3/IL-8 score. In conclusion, MCP-3 and IL-8 were the determinant cytokines driving severe cytokine storm. The MCP-3/IL-8 score provided a potentially clinically meaningful risk strata able to compute the severity of cytokine storm and distinguish COVID-19 patients with fatal clinical outcome. Thus, Applicant has identified determinant cytokines in severe cytokine storm, for example the MCP-3/IL-8 score, that may offer a clinically meaningful risk strata for clinical management by providing a uniform standard to evaluate the severity of cytokine storm at individual patient setting, and distinguishing patients with fatal clinical outcome. Preliminary data suggested the lower ratio of IFNα2/IFNγ might increase the MCP-3/IL-8 score. Applicant's findings advance previous work and help to optimize current clinical management of COVID-19.

Example 2. Elevated Serum Levels of S100A8/A9 and HMGB1 at Hospital Admission are Correlated with Inferior Clinical Outcomes in COVID-19 Patients COVID-19 is a disease with heterogeneous clinical appearances Most patients are asymptomatic or exhibit mild to moderate symptoms; approximately 15% progress to severe pneumonia and about 5% are eventually admitted to the intensive care unit (ICU) due to acute respiratory distress syndrome (ARDS), septic shock and/or multiple organ failure. ICU patients respond poorly to currently available treatments and exhibit a high mortality rate.[1-3] Inadequate identification of the determinants of fatal outcomes is one of the major obstacles to the improvement of the outcomes in severe COVID-19 patients. A previous study reported a scoring system (COVID-GRAM) which accurately predicted the occurrence of critical illness in hospitalized COVID-19 patients.[4] Damage-associated molecular patterns (DAMPs), or alarmins, are a number of molecules, released by stressed cells undergoing microbial infection or sterile injury, that act as danger signals to promote and exacerbate the inflammatory response.[5,6] Of note, the serum level of S100A8/A9 and HMGB1 was found to be correlated with both the severity of pathogen-associated tissue damage and excessive cytokine storm.[7] S100A8 is a calcium- and zinc-binding protein which plays a prominent role in the regulation of inflammatory processes and immune response. It can induce neutrophil chemotaxis and adhesion, and is predominantly found as calprotectin (S100A8/A9) which has a wide plethora of intra- and extracellular functions.

Despite the hypothesis that S100A8/A9 and HMGB1 are significantly involved in COVID-19, so far, no study has yet tried to substantiate the hypothesis. In this study, Applicant aimed to define the role of S100A8/A9 and HMGB1 in progression to a fatal outcome and develop clinically relevant risk strata for COVID-19 patients. A total of 121 patients were enrolled in this retrospective study, of which 40 patients were in ICU and 81 patients in general wards at enrollment (Table S1). ICU Patients had much higher COVID-GRAM risk scores in comparison to those in general wards. Complications, including ARDS, sepsis, septic shock, secondary infection, acute renal injury, acute cardiac injury or failure, were more frequent in COVID-19 patients admitted to ICU. As of the cutoff date of Apr. 30, 2020, most of non-ICU patients (96.3%) had been discharged alive, while 82.5% of ICU patients had died in ICU.

COVID-19 patients treated in general wards had significantly elevated level of S100A8/A9 (P=0.033) but not HMGB1 (P>0.9999) as compared to healthy controls, suggesting that S100A8/A9 is a more sensitive alarmin than HMGB1 in response to SARS-CoV-2 infection. However, both S100A8/A9 and HMGB1 were significantly elevated extracellularly in ICU-admission patients compared to non-ICU patients, or in fatal outcomes patients compared to alive patients (FIG. 8a-d), indicating that significant elevation of S100A8/A9 and HMGB1 was associated with high mortality.

Applicant further examined the Spearman's correlation between the serum S100A8/A9 or HMGB1 levels and clinical manifestations in COVID-19 patients. First of all, either serum levels of S100A8/A9 or HMGB1 at admission were positively correlated with peak CT score and oxygen demand, which is indicative of the severity of acute lung injury and ARDS (FIGS. 8e, f and 9 (S1)a, b). Moreover, the degree of organic impairment, as evaluated by the MCP classification, NTproBNP level, cTn I level, and AKI stage were well correlated with the serum levels of S100A8/A9 or HMGB1 (FIG. 9 (S1)c-j). The level of peak D-dimer significantly was elevated as the serum S100A8/A9 or HMGB1 increased (FIG. 1g, h). On the other hand, the ratio of neutrophils to lymphocytes was positively correlated with the serum S100A8/A9 but not with HMGB1, suggesting S100A8/A9 plays a more important role in the substantial reduction of the peripheral lymphocytes. The serum S100A8/A9 was strongly correlated with the qSOFA score,[8] a quick indicator of sepsisrelated organ dysfunction, indicating that patients with higher S100A8/A9 or HMGB1 levels tended to suffer from more severe sepsis-related organ dysfunction (both P<0.0001) (FIG. 8i-l).

Figure 8:
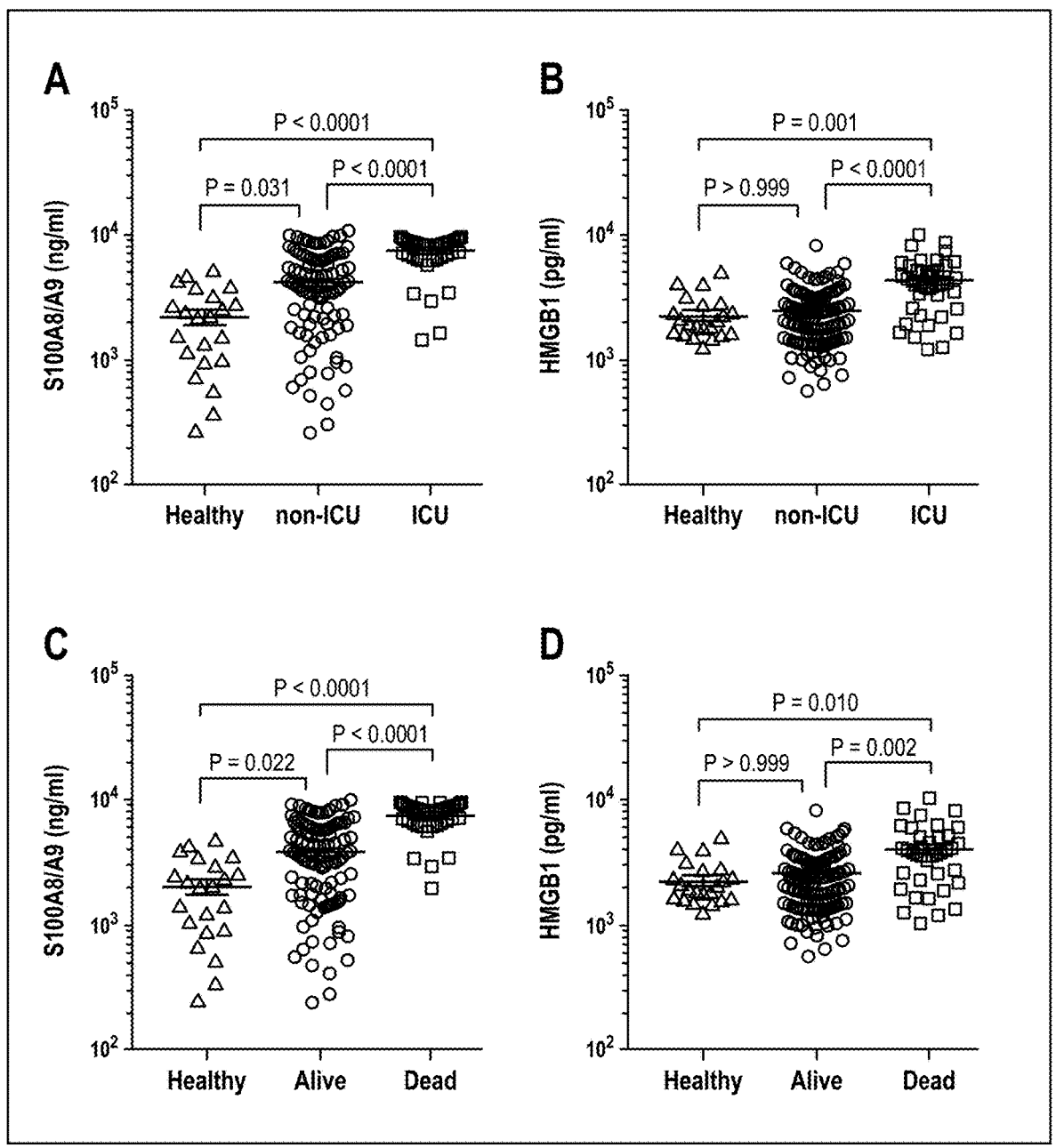
FIG. 8. Serum levels of S100A8/A9 and HMGB1 were strongly correlated with the severity of clinical manifestations and with great predictive power for the risk for ICU admission and death. (a, b) Comparison of S100A8/A9 and HMGB1 levels between healthy people, non-ICU patients, and ICU patients of COVID-19. (c, d) Comparison of S100A8/A9 and HMGB1 levels between healthy people, alive patients and dead patients of COVID-19. Spearman's correlation analyses between S100A8/A9 or HMGB1 levels and peak CT score (e, f), D-dimer level (g, h), neutrophil/lymphocyte ratio (i, j), and quick Sequential Organ Failure Assessment (qSOFA) scores (k, l). (m, n) Spearman's correlation analyses of S100A8/A9 or HMGB1 and COVID-GRAM risk score. (o, p) Comparison of S100A8/A9 or HMGB1 between healthy people and COVID-19 patients of different risk groups (divided according to COVID-GRAM risk score). (q, r) Receiver operating characteristic (ROC) curve evaluation of the performance of S100A8/A9, HMGB1, combined S100A8/A9 and HMGB1, and COVID-GRAM risk score in distinguish COVID-19 patients with ICU admission or subsequent death. Sixty days survival is shown for patients with different circulating S100A8/A9 levels (s) and different COVID-GRAM risks (t) by Kaplan-Meier curves.
Figure 8:
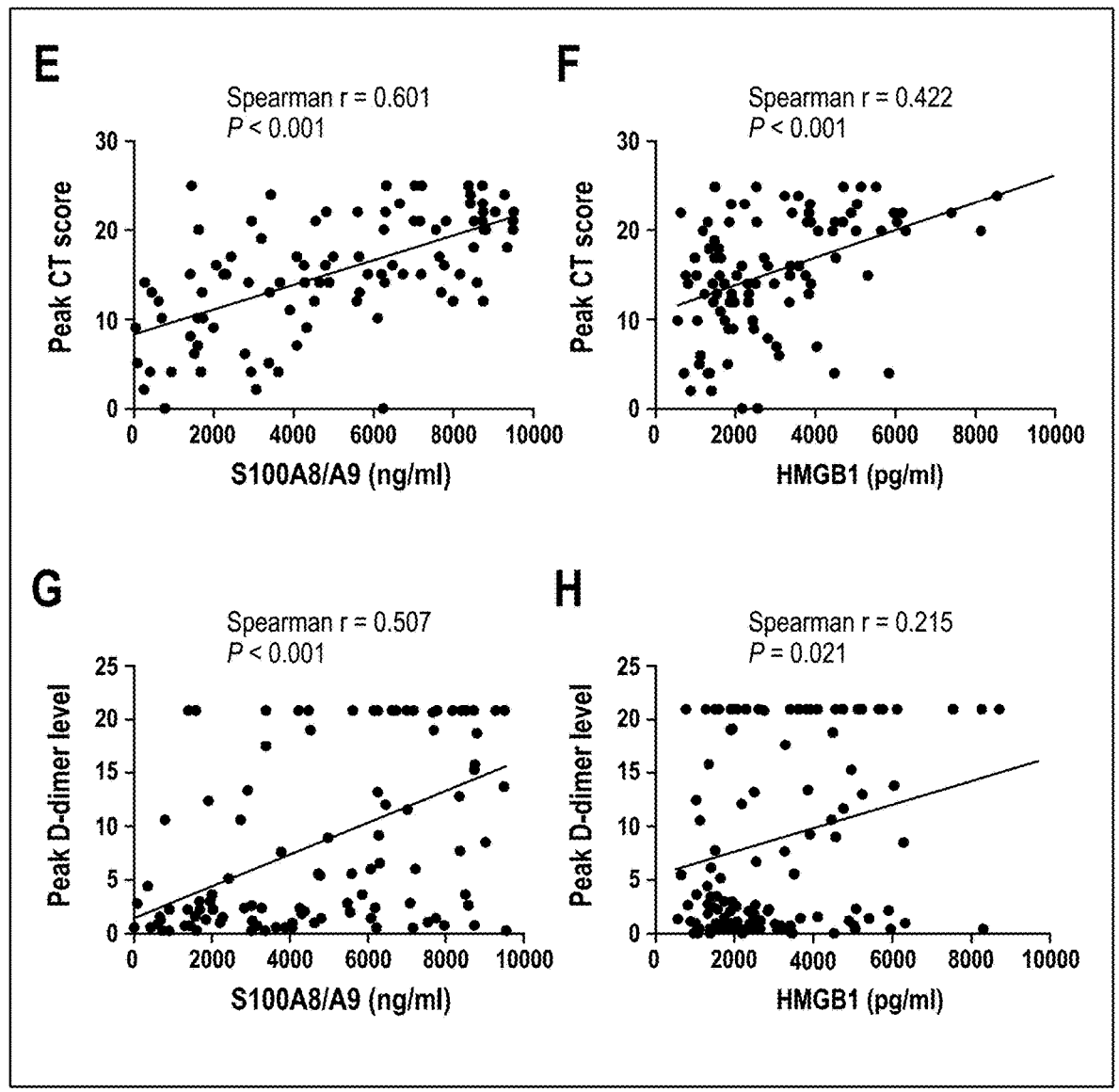
Figure 8:
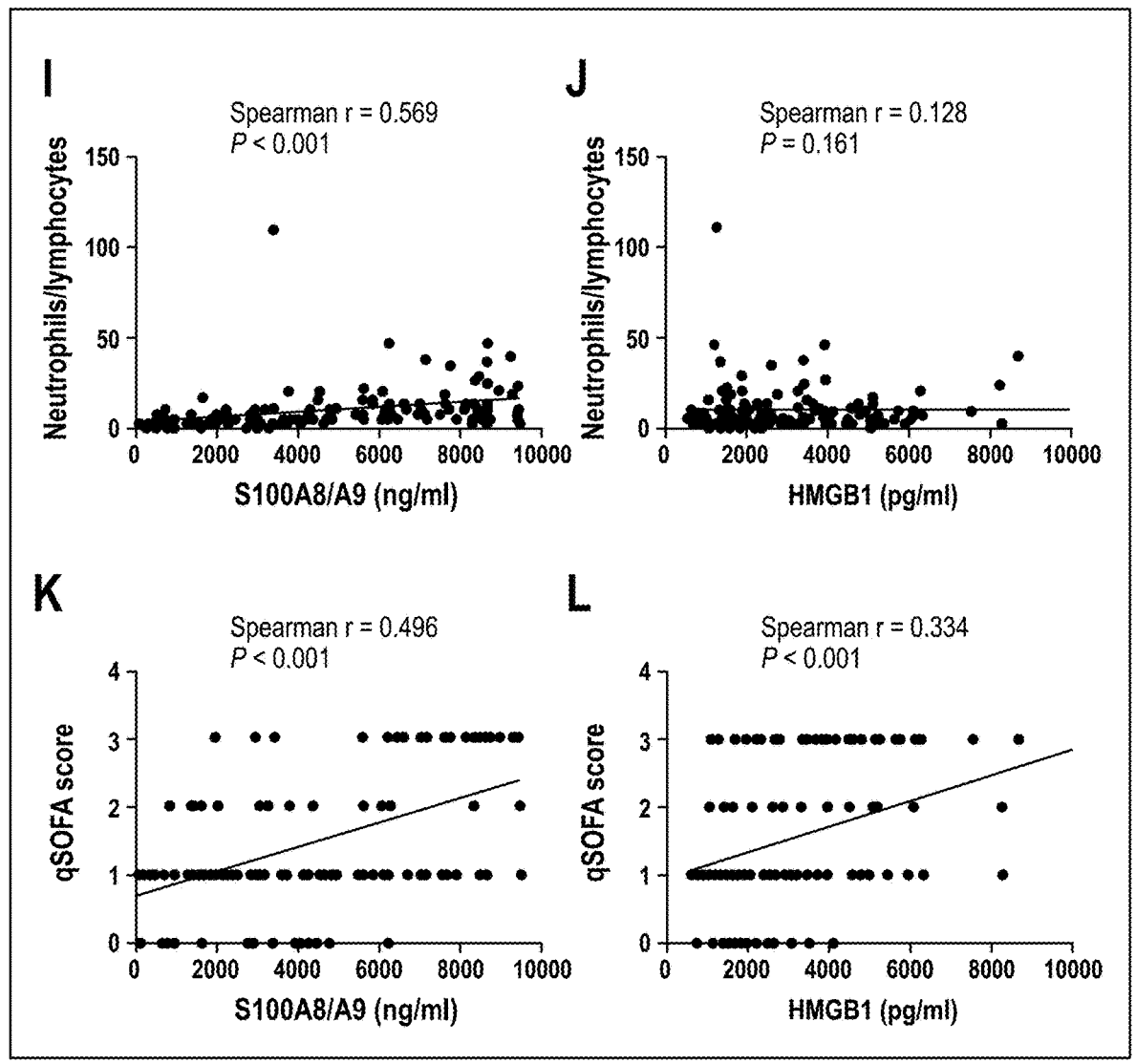
Figure 8:
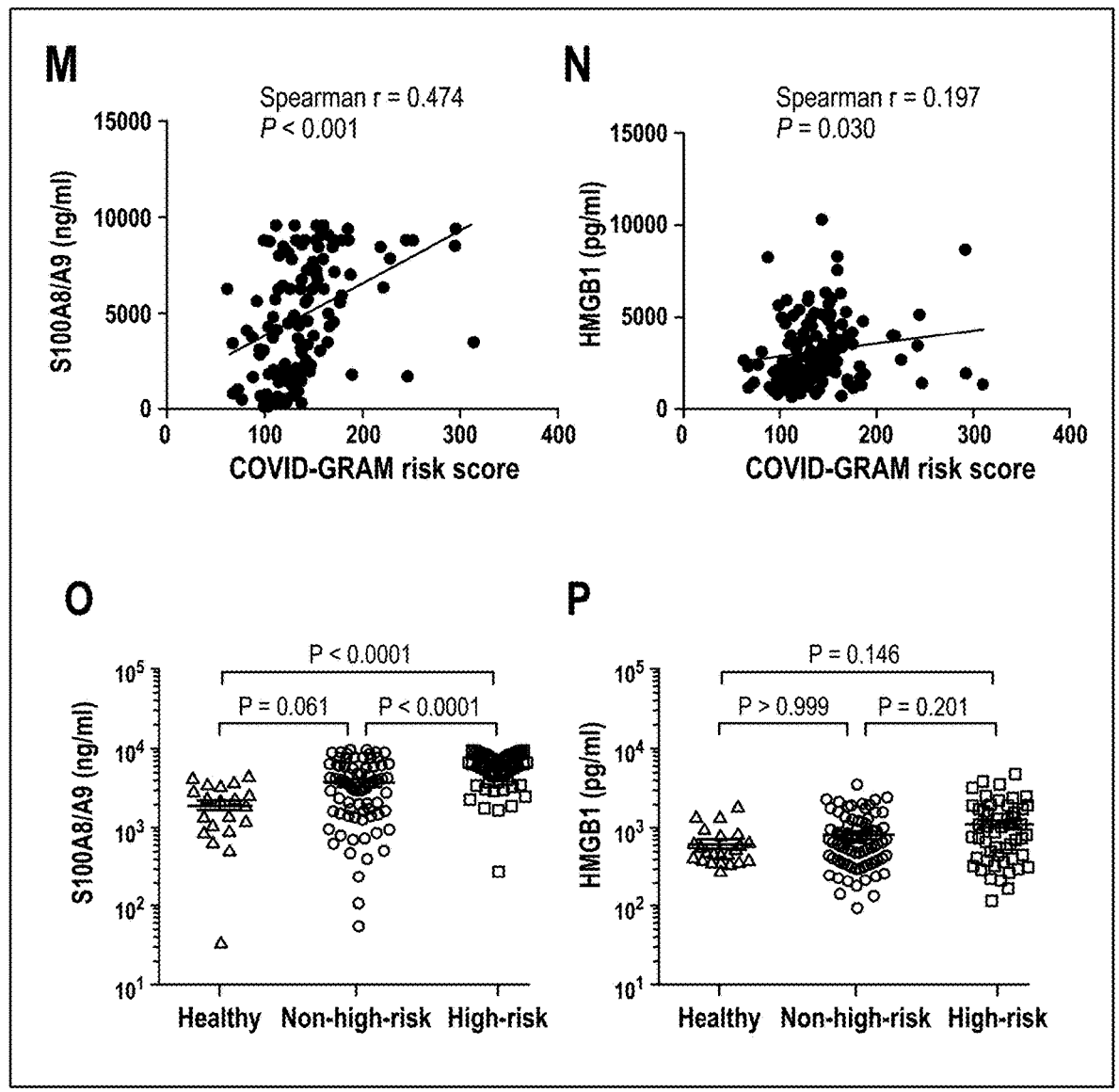
Figure 8:
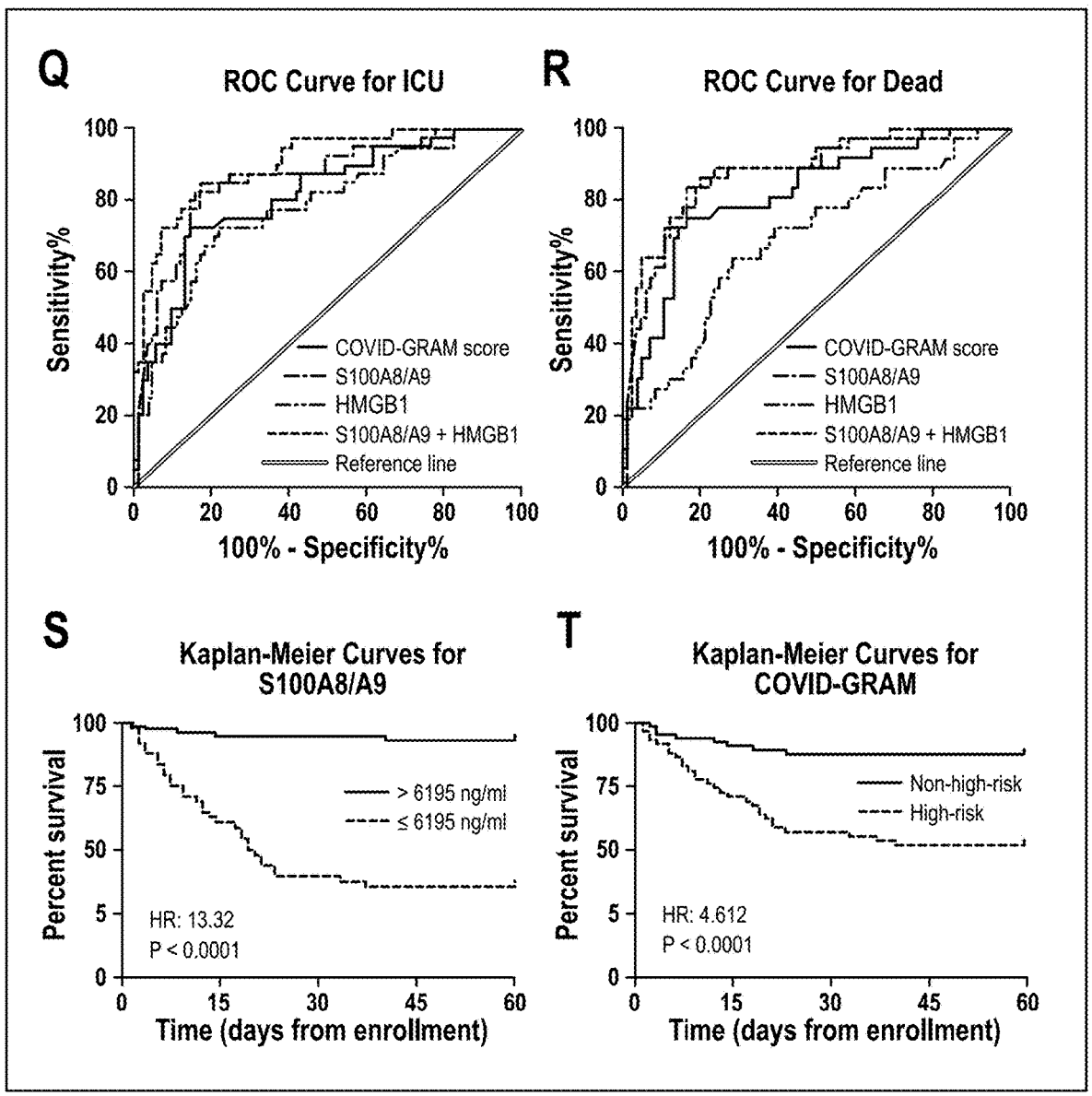
Figure 9:
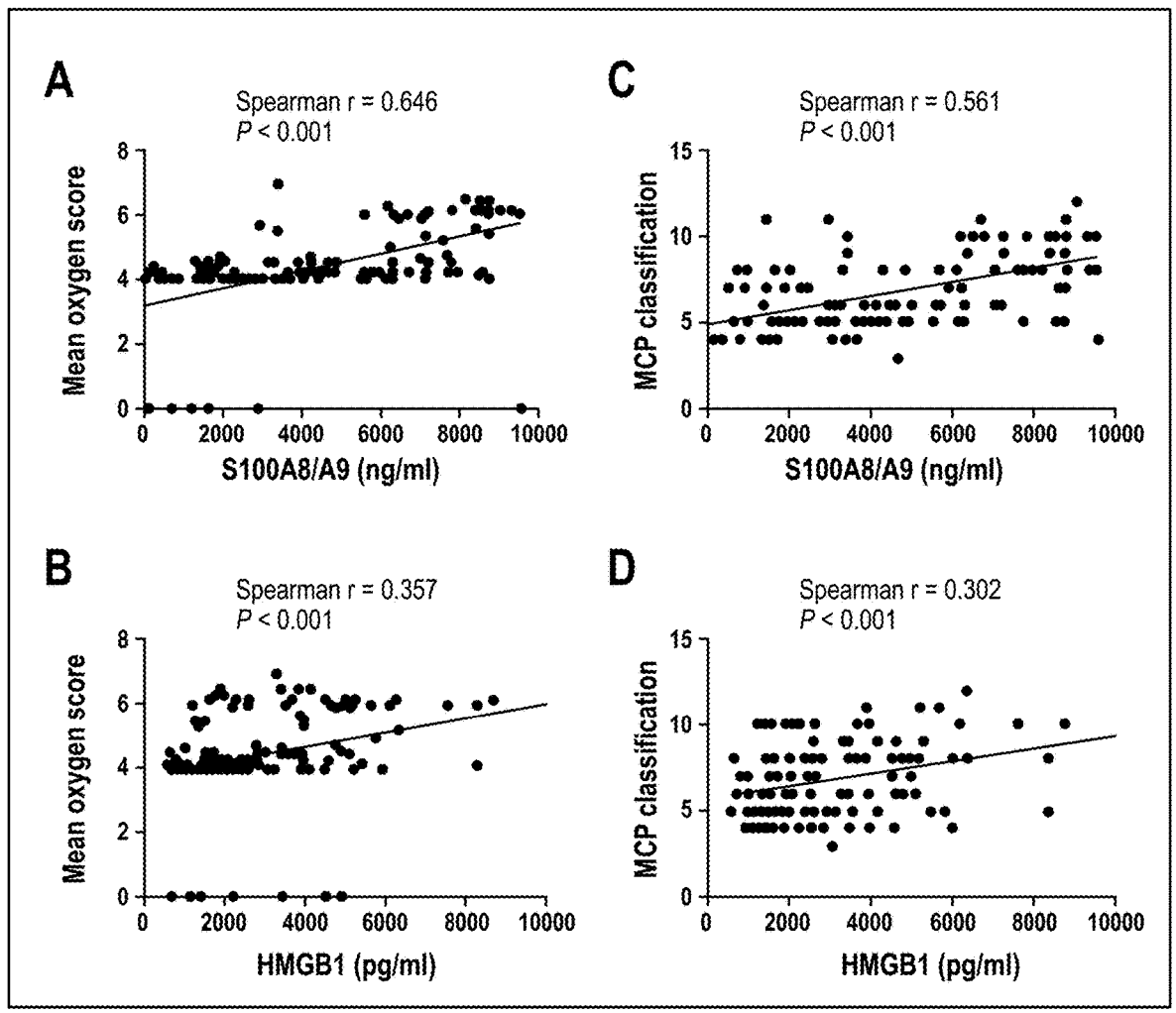
FIG. 9. Serum level of S100A8/A9 and HMGB1 was strongly correlated with the severity of clinical manifestations. Spearman's correlation analyses of S100A8/A9 and mean oxygen score which reflects patients' oxygen-support requirements (a, b), Modified Child-Pugh (MCP) classification which reflects hepatic function (c, d), cardiac biomarkers NT-proBNP and High-sensitive cardiac troponin I (cTn I) (e-h), and AKI stage according to KDIGO clinical practice guidelines (i, j).
Figure 9:
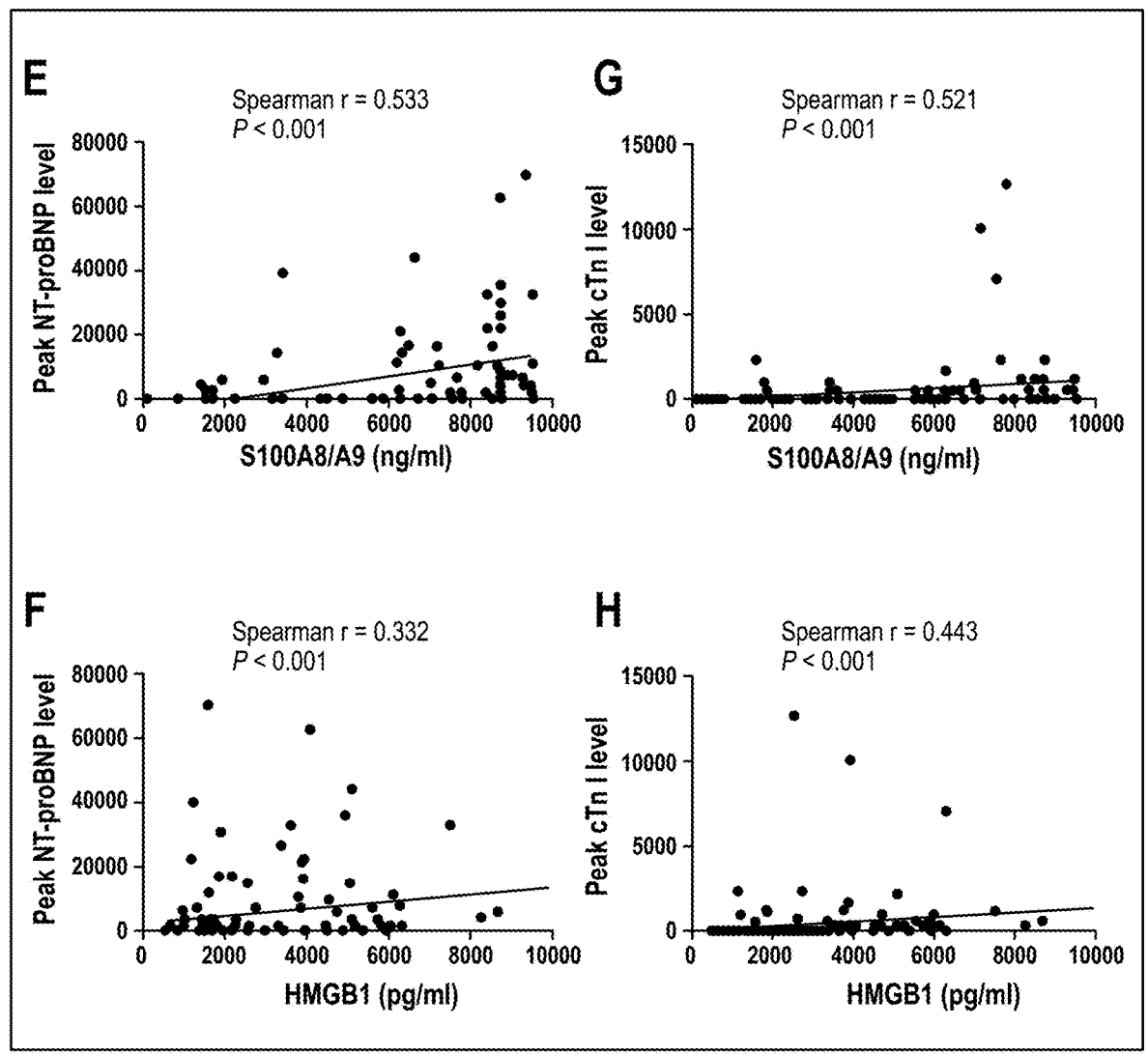
Figure 9:
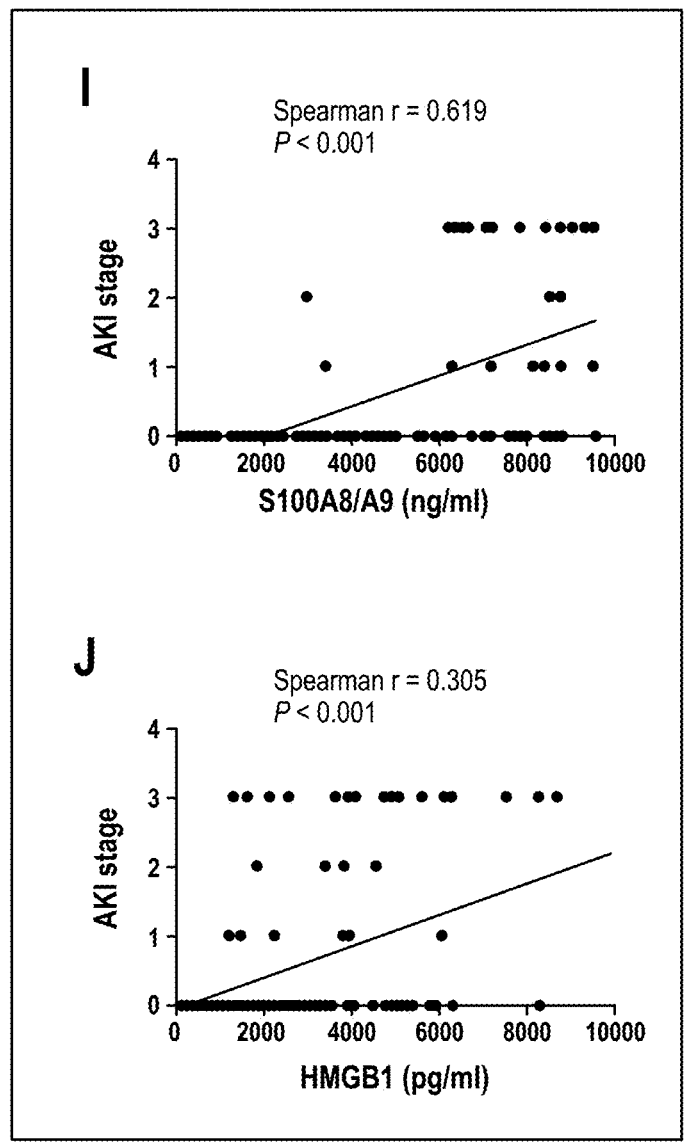

Applicant then evaluated the potential correlation between levels of S100A8/A9 or HMGB1 and COVID-GRAM risk scores. Either levels of S100A8/A9 (P<0.0001) or HMGB1 (P=0.030) significantly correlated with the COVID-GRAM risk scores (FIG. 8m, n). Serum levels of S100A8/A9 but not HMGB1 were significantly increased in patient with high risk of COVID-GRAM risk scores which were defined according to the online calculator (http://118.126.104.170)[4] (FIG. 8o, p), highlighting that S100A8/A9 is a better prognostic indicator than HMGB1.

The prognostic values of S100A8/A9, HMGB1 or COVID-GRAM risk scores were further evaluated by ROC analysis and their areas under curve were calculated (FIG. 8q, r). For the prediction of ICU admission, the AUCs for COVID-GRAM risk scores with S100A8/A9, HMGB1 and S100A8/A9 and HMGB1 in combination were 0.810, 0.860, 0.781 and 0.901, respectively (Table S2). For the prediction of subsequent death, the AUCs for COVID-GRAM risk scores, S100A8/A9, HMGB1 and S100A8/A9 and HMGB1 in combination were 0.818, 0.875, 0.694 and 0.881, respectively (Table S2). The sensitivity and specificity of S100A8/A9 and HMGB1 of the ROC curves illustrated in FIG. 8q, r were listed in Table S2. The combination of S100A8/A9 with HMGB1 increased the prediction power compared to S100A8/A9 or HMGB1 alone although no significant differences were observed statistically (Table S2). Moreover, higher S100A8/A9 level (P<0.0001) or higher COVIDGRAM risk score (P<0.0001) resulted in significant worse overall survival (FIG. 8s, t). The COVID-19 patients were classified into low or high level groups according to the concentrations of S100A8/A9 at a cutoff of 6195 ng/ml, which was set by maximizing Youden's index according to the ROC curves (FIG. 8s). Meanwhile, the COVID-19 patients were also classified into high-risk or nonhigh-risk groups according to COVID-GRAM risk scores (FIG. 8t). The hazard ratio of high S100A8/A9 level was 13.32, which was greater than that of COVID-GRAM risk score (HR=4.612). The concentrations of S100A8/A9 measured at hospital admission showed better predictive power than COVID-GRAM risk scores for subsequent death in COVID-19 patients.

To explore the possible correlation between S100A8/A9 or HMGB1 and cytokine storm in COVID-19, the serum levels of S100A8/A9 or HMGB1 were analyzed by Spearman's correlation tests to know their correlation with of each of the 48 cytokine concentrations in individual patients (Table S3). While the serum levels of S100A8/A9 or HMGB1 correlated with the concentrations of a different spectrum of pro-inflammatory cytokines, 12 cytokines, including IL-8, MCP-3, MCP-1, IL-1rα, β-NGF, IL-7, IL-10, RANTES, G-CSF, IL-1α, CTACK and IL-17A, simultaneously correlated with both the S100A8/A9 and HMGB1. Interestingly, 3 myeloid chemokines, IL-8, MCP-3 and MCP-1, were among the most significant cytokines simultaneously correlated with both the S100A8/A9 and HMGB1 and showed the lowest P value (P<0.0001), indicating that the overproduced S100A8/A9 and HMGB1 in serum were associated with distinct signatures for cytokine storm in patients with COVID-19.[9,10]

In conclusion, Applicant identified two alarmins, especially S100A8/A9, could accurately identify patients who were subsequently admitted to ICU wards or died with a predictive precision similar to or better than COVID-GRAM risk score. Taking S100A8/A9 as a predictor for COVID-19 might offer some advantages over other clinical or laboratory indicators, since it is easy to measure and the result is easy to interpret. As a single parameter alone, to our knowledge, S100A8/S100A9 is the only one helpful for an early identification of COVID-19 patients who may be admitted to ICU admission or facing death. Using S100A8/A9 to distinguish COVID-19 patients with fatal outcomes is of great clinical significance.

Example 2 Methods

Study design and participants. Between Jan. 18 to Mar. 3, 2020, 121 patients with COVID-19 were enrolled into this prospective study, including 40 admitted to ICU and 81 treated on general wards. Diagnosis of COVID-19 was established according to the WHO guidance[1]. Healthy controls (N=22) were also included. This study was approved by the Medical ethics committee of Tongji Hospital, Tongji Medical College, Huazhong University of Science and Technology, Wuhan, China (IRB ID: TJ-C20200114). Written informed consent was obtained from all patients, and waived if the patient was too unwell to provide it under an emerging infectious disease provision. Exclusion criteria included: (1) no clinical data and chest radiographic findings were available; (2) no written informed consent could be obtained; (3) patients had received remdesivir or were involved in other clinical trials.

Clinical samples and information collection. Serum samples were prospectively collected within the first 72 h of hospitalization from patients with COVID-19 in ICU or non-ICU wards and healthy donors. Blood samples were collected and immediately transferred to a 4° C. refrigerator and processed within 24 hours. Serum samples were harvested using a serum separator tube (SST) and allowed to coagulate for 30 minutes at room temperature before centrifugation for 15 minutes at 1,000×g. The serum was collected and assayed immediately or aliquoted, and samples were stored at ≤−80° C. Repeated freeze-thaw cycles were avoided. Clinical data were inputted into an electronic data capture system (EDCS), including demographics, medical history, oximetric measurements, CT scans, swabs monitoring, treatments received, clinical outcomes, laboratory findings (complete blood count, serum biochemical parameters, D-dimer etc.)

Definitions

Septic shock and sepsis were confirmed in accordance with the 2016 Third International Consensus Definition for Sepsis and Septic Shock. Secondary infection was diagnosed when a patient presented clinical symptoms or signs of infections and culture of samples from lower respiratory tract, blood, urine or stool, showed that the patient was positive for new a pathogen after admission[2]. Acute kidney injury was diagnosed according to the KDIGO clinical practice guidelines' and acute cardiac injury was diagnosed if serum level of cardiac biomarker (e.g. high-sensitive cardiac troponin I was above the 99$^{th}$ percentile upper reference limit) was abnormal. Acute heart failure was defined on the basis of the serum NT-proBNP level in different age groups and acute respiratory distress syndrome (ARDS) was confirmed against the Berlin Definition[4, 5]. The virus clearance time was defined as the time from enrollment to the first day of two consecutive negative results of RT-PCR assay of either oropharyngeal or nasopharyngeal swabs, at least 24 h apart[6]. The D-D dimer level in each patient was assessed weekly from enrollment to discharge[7]. For each patient, the highest D-D dimer level was defined as the peak D-D dimer level and was used in later analysis.

Assessment of Acute Lung Injury, Multiple Organic Impairment and COVID-GRAM Risk Score Non-contrast enhanced chest CT scans were performed weekly, and when necessary, additional scans were also conducted. A semi-quantitative scoring system was employed to assess the lung involvement as previously described[8]. The peak score of each patient was extracted and included further analysis. Data on patients' change in oxygen-support requirement were rated daily from enrollment to discharge on a seven-category ordinal scale[9]. Patients scoring less than 3 were deemed as having no need for oxygenation. For each patient, the mean score in oxygen-support requirement (MOSR) was calculated by using the following formula:

$$MOSR = \frac{\sum_{i=4}^{7} i \times n_i}{\sum_{i=4}^{7} n_i}$$

Modified Child-Pugh (MCP) classification[10] and quick Sequential Organ Failure Assessment (qSOFA) scores[11] were obtained and the worst scores were recorded. The COVID-GRAM risk was scored by using an online calculator (http://118.126.104.170)[12]. All 121 patients in our cohort were reviewed and scored independently by two physicians or radiologists who were blinded to the clinical features and alarmins data, and final scores were determined by achieving a consensus.

S100A8/A9 and HMGB1 Measurements.

Serum levels of S100A8/A9 and HMGB1 were measured using the human S100A8/A9 heterodimer immunoassay kit (cat #DS8900, R&D Systems, USA) and human HMGB-1 ELISA kit (Cat #NBP2-62766, Novus Biologicals, Canada), respectively.

Cytokine Measurements.

The levels of serum cytokines were determined by employing Bio-Plex Pro Human Cytokines 48-Plex Screening assay (Bio-Rad Life Sciences, Hercules, Calif., USA) on a Luminex FlEXMAP 3D system (Luminex, Austin, Tex., USA) according to the manufacturer's protocols. The 48-Plex Screening panel: Basic FGF, CTACK, eotaxin, G-CSF, GM-CSF, GRO-α, HGF, ICAM-1, IFN-α2, IFN-γ, IL-1α, IL-1rα, IL-2, IL-2Rα, IL-3, IL-4, IL-5, IL-6, IL-7, IL-8, IL-9, IL-10, IL-12, IL-13, IL-15, IL-16, IL-17A, IL-18, IP-10, LIF, MCP-1, MCP-3, M-CSF, MIF, MIG, MIP-1α, β-NGF, PDGF-BB, RANTES, SCF, SCGF-13, SDF-1α, TNF-α, TNF-β, TRAIL, VCAM-1, VEGF-A. Data were analyzed using the Bio-Plex Manager 6.2 software package (Bio-Rad Life Sciences, Hercules, Calif., USA).

Statistical Analysis.

The misclassification error and the area under curve (AUC) of the receiver operating characteristic curve (ROC) were calculated to assess the performance in the prediction of ICU admission and fatal outcomes, respectively. Youden index was calculated on the basis of the ROC to help set the appropriate cut-off value. Data were analyzed using IBM SPSS Statistics for Windows version 25.0 (IBM Corp., NY, USA) and GraphPad Prism version 7.0 (GraphPad Software Inc., CA, USA). Univariate analyses were assessed with the Utest for continuous values. Multiple comparisons were made by utilizing Dunn's multiple comparisons test. Correlations between immune scores and clinical characteristics were estimated by Spearman's correlation analysis. Survival curves of different groups were analyzed using the Kaplan-Meier method, and differences were compared using the log-rank (Mantel-Cox) test.

TABLE S1

Demographic and Clinical Characteristics of the Patients

| Characteristics | Total (n = 121) | Non-ICU (n = 81) | ICU (n = 40) | P-value |
| --- | --- | --- | --- | --- |
| Age, years | 63 (53-70) | 62 (50-67) | 67 (57-73) | 0.0337 |
| Male, No. (%) | 77 (63.6) | 49 (60.5) | 28 (70.0) | 0.3065 |
| Comorbidity, No. (%) | 75 (62.0) | 48 (59.3) | 27 (67.5) | 0.4300 |
| Hypertension | 46 (38.0) | 33 (40.7) | 13 (32.5) | |
| Diabetes | 27 (22.3) | 19 (23.5) | 8 (20.0) | |
| Coronary artery heart disease | 12 (9.9) | 7 (8.6) | 5 (12.5) | |
| Cancer | 6 (5.0) | 5 (6.2) | 1 (2.5) | |
| COPD | 3 (2.5) | 0 | 3 (7.5) | |
| Immunodeficiency | 2 (1.7) | 1 (1.2) | 1 (2.5) | |
| COVID GRAM risk score | 138 (116-160) | 129 (109-144) | 161 (140-188) | <0.0001 |
| Medium risk | 63 (52.1) | 53 (65.4) | 10 (25.0) | <0.0001 |
| High risk | 58 (47.9) | 28 (34.6) | 30 (75.0) | |
| Time from illness onset to enrollment, days | 20 (14-26) | 20 (13-27) | 21 (17-25) | 0.3708 |
| Treatment, No. (%) | | | | |
| Antibiotics | 104 (86.0) | 65 (80.2) | 39 (97.5) | 0.0108 |
| Antivirals | 111 (91.7) | 75 (92.6) | 36 (90.0) | 0.7285 |
| Intravenous Immunoglobin | 39 (32.2) | 19 (23.5) | 20 (50.0) | 0.0033 |
| Corticosteroids | 87 (71.9) | 50 (61.7) | 37 (92.5) | 0.0002 |
| ECMO | 6 (5.0) | 0 | 6 (15.0) | 0.0010 |
| Renal replacement therapy | 7 (5.8) | 1 (1.2) | 6 (15.0) | 0.0052 |
| Highest level of respiratory support, No. (%) | 53 (43.8) | 13 (16.0) | 40 (100.0) | |
| High-flow nasal cannula oxygen therapy | 5 (4.1) | 5 (6.2) | 0 | |

TABLE S1-continued

Demographic and Clinical Characteristics of the Patients

| Characteristics | Total (n = 121) | Non-ICU (n = 81) | ICU (n = 40) | P-value |
|---|---|---|---|---|
| Non-invasive mechanical ventilation | 10 (8.3) | 6 (7.4) | 4 (10.0) | |
| Invasive mechanical ventilation | 38 (31.4) | 2 (2.5) | 36 (90.0) | |
| qSOFA score | 1 (1-3) | 1 (1-1) | 3 (2-3) | <0.0001 |
| 0 | 15 (12.4) | 15 (18.5) | 0 | |
| 1 | 56 (46.3) | 53 (65.4) | 3 (7.5) | |
| 2 | 18 (14.9) | 11 (13.6) | 7 (17.5) | |
| 3 | 32 (26.4) | 2 (2.5) | 30 (75.0) | |
| MCP classification | 7 (5-8) | 5 (5-7) | 10 (8-10) | <0.0001 |
| MCP1 | 17 (14.0) | 17 (21.0) | 0 | |
| MCP2 | 26 (21.5) | 25 (31.0) | 1 (2.5) | |
| MCP3 | 78 (64.5) | 39 (48.0) | 39 (97.5) | |
| Complications, No. (%) | | | | |
| Sepsis | 50 (41.3) | 13 (16.0) | 37 (92.5) | <0.0001 |
| Septic Shock | 31 (25.6) | 0 | 31 (77.5) | <0.0001 |
| Secondary infection | 10 (8.3) | 1 (1.2) | 9 (22.5) | 0.0002 |
| Acute kidney injury | 32 (26.4) | 1 (12) | 31 (77.5) | <0.0001 |
| Acute cardiac injury | 50 (41.3) | 10 (12.3) | 40 (100.0) | <0.0001 |
| Acute heart failure | 39 (32.2) | 12 (14.8) | 39 (96.0) | <0.0001 |
| ARDS | 38 (31.4) | 2 (2.5) | 36 (90.0) | <0.0001 |
| Clinical outcome at data cutoff, No. (%) | | | | <0.0001 |
| Discharged alive | 83 (68.6) | 78 (96.3) | 5 (12.5) | |
| Died | 36 (29.8) | 3 (3.7) | 33 (82.5) | |
| Hospitalization | 2 (1.7) | 0 | 2 (5.0) | |

Data include median (IQR), n (%), ICU intensive care unit; COPD: chronic obstructive pulmonary disease; COVID coronavirus disease; ECMO: extracorporeal membrane oxygenation. qSOFA: quick sequential organ failure assessment; MCP: modified Child-Pugh; ARDS: acute respiratory distress syndrome.

TABLE S2

The discriminatory performance of ROC curves

| Variables | AUC | Sensitivity | Specificity | Cut-off |
|---|---|---|---|---|
| Non-ICU versus ICU | | | | |
| GRAM risk score | 0.810 | 72.5% | 85.2% | 149.550 |
| S100A8/A9 | 0.860 | 85.0% | 82.7% | 6195.015 |
| HMGB1 | 0.781 | 72.5% | 77.8% | 3273.618 |
| S100A8/A9 + HMGB1 | 0.901 | 77.5% | 87.7% | 0.452 |
| Alive versus Dead | | | | |
| GRAM risk score | 0.818 | 75.0% | 83.5% | 149.550 |
| S100A8/A9 | 0.875 | 83.3% | 83.5% | 6284.175 |
| HMGB1 | 0.694 | 63.9% | 71.8% | 3273.618 |
| S100A8/A9 + HMGB1 | 0.881 | 88.9% | 76.5% | 0.245 |

ROC: receiver operating characteristic; AUC: under the ROC curve.

Bold texts of variables indicate state variables and regular texts of variables indicate test variables

TABLE S3

Spearman's correlation of serum levels of S100A8/A9 or HMGB1 with the concentrations of cytokines.

| Analyte | S100A8/A9 P-value | HMGB-1 P-value |
|---|---|---|
| IL-8 | *<0.0001* | *<0.0001* |
| MCP-3 | *<0.0001* | *<0.0001* |
| MCP-1 | *<0.0001* | *0.0006* |
| IL-1ra | *<0.0001* | *0.0305* |
| IL-6 | *<0.0001* | 0.0511 |
| HGF | *<0.0001* | 0.338 |
| IL-16 | *0.0002* | 0.1591 |
| β-NGF | *0.0003* | *0.0042* |
| IL-7 | *0.0013* | *0.0001* |
| IL-10 | *0.0025* | *<0.0001* |
| RANTES | *0.0084** | *0.0001** |
| G-CSF | *0.011* | *<0.0001* |
| IL-1α | *0.0128* | *<0.0001* |
| MIF | *0.0227* | 0.5143 |
| CTACK | *0.0326** | *0.0016** |
| IL-17A | *0.0347* | *0.0002* |
| IL-9 | 0.0829 | *0.0003** |
| TNF-β | 0.0895 | *0.0016** |
| MIG | 0.1438 | *0.0006* |
| IL-12 (p40) | 0.1539 | *0.0391* |
| MIP-1β | 0.2299 | *0.0027** |
| IL-4 | 0.3048 | *0.0009** |
| GRO-α | 0.3067 | *0.001** |
| IL-12 (p70) | 0.6947 | *0.011* |
| PDGF-BB | 0.9328 | *0.0114** |

Bold text indicates P-values < 0.05. Italicized cells represent positive correlation and cells marked with
* represent negative correlation.

Example 2 References

1. World Health O. Clinical management of severe acute respiratory infection when novel coronavirus (2019-nCoV) infection is suspected: interim guidance, 28 Jan. 2020. Geneva: World Health Organization; 2020 2020. Contract No.: WHO/nCoV/Clinical/2020.3.

2. Huang C, Wang Y, Li X, Ren L, Zhao J, Hu Y, et al. Clinical features of patients infected with 2019 novel coronavirus in Wuhan, China. Lancet (London, England). 2020; 395(10223):497-506.
3. Khwaja A. KDIGO clinical practice guidelines for acute kidney injury. Nephron Clinical practice. 2012; 120(4): c179-84.
4. [Chinese guidelines for the diagnosis and treatment of heart failure 2018]. Zhonghua xin xue guan bing za zhi. 2018; 46(10):760-89.
5. Ranieri V M, Rubenfeld G D, Thompson B T, Ferguson N D, Caldwell E, Fan E, et al. Acute respiratory distress syndrome: the Berlin Definition. Jama. 2012; 307(23): 2526-33.
6. Cao Y, Wei J, Zou L, Jiang T, Wang G, Chen L, et al. Ruxolitinib in treatment of severe coronavirus disease 2019 (COVID-19): A multicenter, single-blind, randomized controlled trial. The Journal of allergy and clinical immunology. 2020.
7. Zhang L, Yan X, Fan Q, Liu H, Liu X, Liu Z, et al. D-dimer levels on admission to predict in-hospital mortality in patients with Covid-19. Journal of thrombosis and haemostasis: JTH. 2020.
8. Pan F, Ye T, Sun P, Gui S, Liang B, Li L, et al. Time Course of Lung Changes at Chest CT during Recovery from Coronavirus Disease 2019 (COVID-19). Radiology. 2020; 295(3):715-21.
9. Cao B, Wang Y, Wen D, Liu W, Wang J, Fan G, et al. A Trial of Lopinavir-Ritonavir in Adults Hospitalized with Severe Covid-19. N Engl J Med. 2020; 382(19):1787-99.
10. Wen X, Yao M, Lu Y, Chen J, Zhou J, Chen X, et al. Integration of Prealbumin into Child-Pugh Classification Improves Prognosis Predicting Accuracy in HCC Patients Considering Curative Surgery. Journal of clinical and translational hepatology. 2018; 6(4):377-84.
11. Rudd K E, Seymour C W, Aluisio A R, Augustin M E, Bagenda D S, Beane A, et al. Association of the Quick Sequential (Sepsis-Related) Organ Failure Assessment (qSOFA) Score With Excess Hospital Mortality in Adults With Suspected Infection in Low- and Middle-Income Countries. Jama. 2018; 319(21):2202-11.
12. Liang W, Liang H, Ou L, Chen B, Chen A, Li C, et al. Development and Validation of a Clinical Risk Score to Predict the Occurrence of Critical Illness in Hospitalized Patients With COVID-19. JAMA internal medicine. 2020.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. All accessioned information (e.g., as identified by PUBMED, PUBCHEM, NCBI, UNIPROT, or EBI accession numbers) and publications in their entireties are incorporated into this disclosure by reference in order to more fully describe the state of the art as known to those skilled therein as of the date of this disclosure. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method of treating an individual having, or suspected of having, a SARS-Cov-2 infection (COVID-19), comprising
   a. detecting, via enzyme linked immunosorbent assay (ELISA), a protein level of calprotectin (S100A8/A9) in a sample obtained from said individual, said sample being a serum sample;
   b. comparing said calprotectin (S100A8/A9) protein level to that of a healthy control;
   c. determining the risk that said individual will require intensive care unit (ICU) care based on the levels of said calprotectin (S100A8/A9) and on said comparing; and
   d. administering a therapeutically effective amount of ruxolitinib to an individual determined to have an increased risk of requiring intensive care unit (ICU) care.

2. The method of claim 1, wherein an increase in S100A8/A9 as compared to said healthy control indicates that said individual has an increased risk of requiring ICU care.

3. The method of claim 1, wherein said individual presents with cytokine storm.

4. The method of claim 1, wherein said ruxolitinib is administered at a dosage of about 10 mg/day, or about 15 mg/day, or about 20 mg/day, or about 25 mg/day, or about 30 mg/day, or about 35 mg/day, or about 40 mg/day, or about 45 mg/day, or about 50 mg/day, or about 55 mg/day, or about 60 mg/day, or about 65 mg/day, or about 70 mg/day, or about 75 mg/day, or about 80 mg/day, or about 85 mg/day, or about 90 mg/day, or from about 10 to about 100 mg/day, or about 25 to about 75 mg per day, or about 30 to 50 mg/day, or from about 100 to about 200 mg/day, or greater than 200 mg/day.

* * * * *